(12) United States Patent
Qureshi et al.

(10) Patent No.: US 11,221,321 B2
(45) Date of Patent: Jan. 11, 2022

(54) LIQUID CHROMATOGRAPHIC METHOD FOR THE SIMULTANEOUS ANALYSIS OF ANTIHYPERTENSIVE AND ANTILIPIDEMIC AGENTS AND INTERACTIONS THEREOF

(71) Applicant: Imam Abdulrahman Bin Faisal University, Dammam (SA)

(72) Inventors: Faiza Qureshi, Dammam (SA); Muhammad Nawaz, Dammam (SA)

(73) Assignee: Imam Abdulrahman Bin Faisal University, Dammam (SA)

(*) Notice: Subject to any disclaimer, the term of this patent is extended or adjusted under 35 U.S.C. 154(b) by 387 days.

(21) Appl. No.: 16/425,668

(22) Filed: May 29, 2019

(65) Prior Publication Data
US 2020/0378942 A1    Dec. 3, 2020

(51) Int. Cl.
| | |
|---|---|
| *G01N 33/15* | (2006.01) |
| *B01D 15/32* | (2006.01) |
| *B01D 15/22* | (2006.01) |
| *C07D 257/04* | (2006.01) |
| *A61K 31/41* | (2006.01) |
| *A61K 31/366* | (2006.01) |
| *C07D 309/30* | (2006.01) |
| *G01N 21/33* | (2006.01) |

(52) U.S. Cl.
CPC .......... *G01N 33/15* (2013.01); *A61K 31/366* (2013.01); *A61K 31/41* (2013.01); *B01D 15/22* (2013.01); *B01D 15/325* (2013.01); *C07D 257/04* (2013.01); *C07D 309/30* (2013.01); *G01N 21/33* (2013.01)

(58) Field of Classification Search
CPC ...... G01N 21/33; G01N 33/15; A61K 31/366; A61K 31/165; A61K 31/40; A61K 31/403; A61K 31/41; A61K 31/415; A61K 31/416; A61K 31/4178; A61K 45/06; B01D 15/22; B01D 15/325; B01J 31/22; C07B 53/00; C07C 13/72; C07C 231/12; C07C 233/51; C07C 39/17; C07C 43/21; C07C 43/225; C07D 257/04; C07D 309/30; C07F 9/6571
See application file for complete search history.

(56) References Cited

U.S. PATENT DOCUMENTS

2018/0370876 A1* 12/2018 Ding ..................... C07C 231/12

FOREIGN PATENT DOCUMENTS

| CN | 104133006 B | 1/2016 |
| CN | 104165937 B | 5/2016 |

(Continued)

OTHER PUBLICATIONS

Bhatia et al., vol. 35 (3), pp. 428-443, Year 2012, RP-HPLC Method for Simultaneous Estimation of Atorvastatin Calcium, Losartan Potassium, Atenolol, and Aspirin From Tablet Dosage Form and Plasma. (Year: 2012).*

(Continued)

*Primary Examiner* — Nimeshkumar D Patel
*Assistant Examiner* — Gedeon M Kidanu
(74) *Attorney, Agent, or Firm* — Oblon, McClelland, Maier & Neustadt, L.L.P.

(57) ABSTRACT

The invention is directed to a precise, accurate and economical method for the simultaneous quantification of amounts of a dissolved sartan and dissolved statin in a mixture containing at least one sartan and at least one statin.

19 Claims, 18 Drawing Sheets

(56) References Cited

FOREIGN PATENT DOCUMENTS

Figure 1:
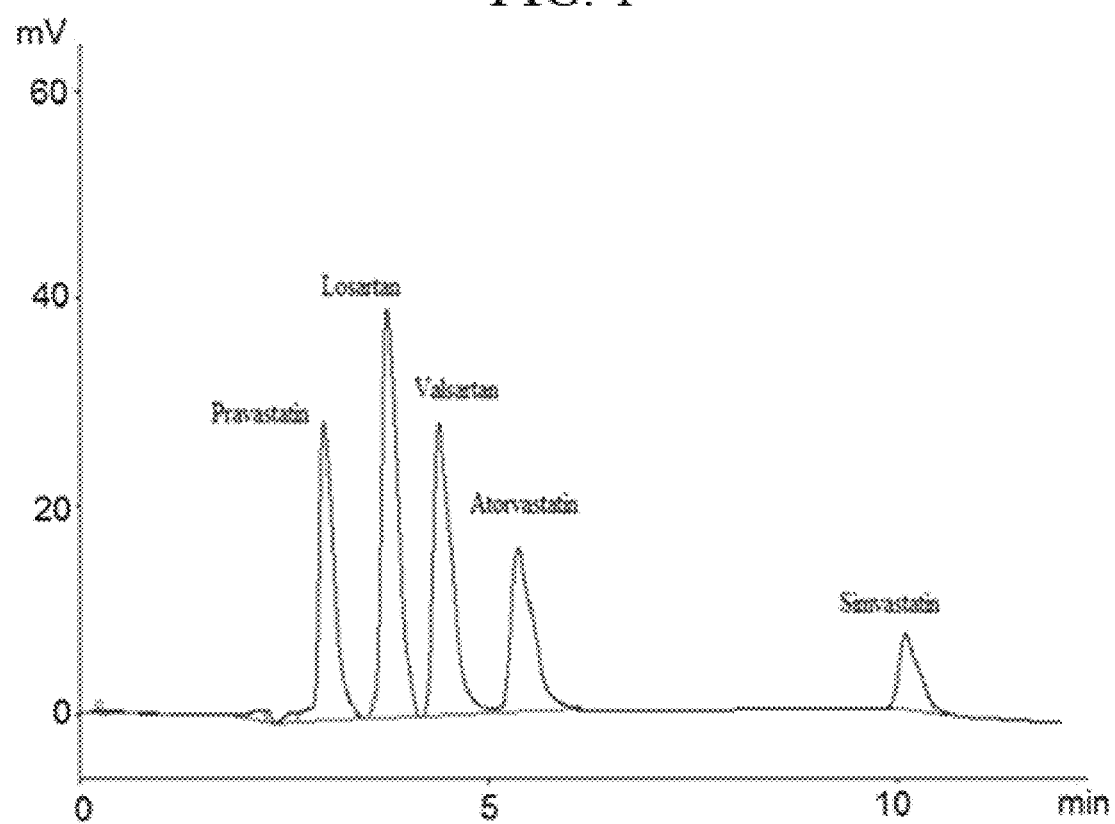

IN        201402536(I3)       4/2016
KR          101774402 B1 *   9/2017   ............. A61K 31/40

OTHER PUBLICATIONS

Iriarte, et al. ; Validation of a fast liquid chromatography—UV method for the analysis of drugs used in combined cardiovascular therapy in human plasma ; Nov. 14, 2017 ; Abstract Only ; 1 Page.

Panchal, et al. ; Simultaneous analysis of atorvastatin calcium and losartan potassium in tablet dosage forms by RPHPLC and HPTLC ; Acta Chromatographica, vol. 22, Issue 2 ; May 25, 2010 ; Abstract Only ; 1 Page.

Ahmed, et al. ; Bioavailability and Interaction Potential of Atorvastatin and Losartan on Co-administration in Healthy Human Subjects ; JBB vol. 1 ; May-Jun. 2009 ; 10 Pages.

Bhatia, et al. ; RP-HPLC Method for Simultaneous Estimation of Atorvastatin Calcium, Losartan Potassium, Atenolol, and Aspirin From Tablet Dosage Form and Plasma ; Journal of Liquid Chromatography Technologies, vol. 35, Issue 3 ; 2012 ; Abstract Only ; 1 Page.

Ozkan, et al. ; Quality Control and Drug Dissolution Studies of Pharmaceutical Preparations Containing Cerivastatin Sodium by Means of RP-HPLC* ; Journal of Liquid Chromatography & Related Technologies, vol. 25, Issue 2 ; 2002 ; Abstract Only ; 1 Page.

\* cited by examiner

LIQUID CHROMATOGRAPHIC METHOD FOR THE SIMULTANEOUS ANALYSIS OF ANTIHYPERTENSIVE AND ANTILIPIDEMIC AGENTS AND INTERACTIONS THEREOF

BACKGROUND OF THE INVENTION

Field of the Invention

The invention falls with the fields of pharmacology and chemistry and involves methods for simultaneously quantifying sartan and statin drugs in a mixture containing both kinds of drugs and for detecting interactions between drugs in the mixture.

Description of Related Art

Intermixing of a sartan drug and a statin drug in a patient is common because these drugs are often coprescribed and taken concurrently. Hypertension (HT), cardiovascular disease (CVD), hyperlipidemia (HL) and hypercholesterolemia (HC) tend to co-occur and are often synergistic, that is, one augmenting the other. While the complex etiologies and biological mechanisms involved are under investigation, the presence of one of these diseases often contributes to development of others and increases the risk of cardiovascular and coronary disease morbidity or mortality.

Concurrent therapy is inevitable for the management of such synergistic conditions. However, with concurrent medication, come concomitant complications, such as drug-drug interaction. For the co-therapy for HT and HC, the optimal treatment recommended by learned therapists entail administration of a) antihypertensive drugs for the treatment of HT, and b) antilipidemic agents a cholesterol lowering agent that block the production of cholesterol in body for treatment of HL and HC. Thus, it is important to be able to assess how different classes of drugs used to treat these conditions interact in order to prescribe a drug combination effective for a particular patient or class of patients.

Bhatia, et al., J. Liq. Chromatogr. Rel. Technol. 35(3): 428-443 (2012), describes an RP-HPLC method for simultaneous detection of atorvastatin calcium (a statin), losartan potassium (a sartan), atenolol and aspirin in plasma. Rahman, et al., J. Pharm. Qual. Assur. 1(1): 25-29 (2015) simultaneously estimates antihypertensive and antidiabetic drugs by HPLC. IN201402536 I3 describes HPLC and UV detection a mixture of chlorzoxazone (a muscle relaxant), atorvastatin (a statin), diclofenac (a NSAID) and efavirenz (anti-HIV drug). CN104165937B and CN104133006B describe HPLC detection of a combination of a blood sugar lowering drug and a blood pressure lowering drug. However, these publications do not consider the problems associated with mixture of a sartan with a statin outside of the blood stream (e.g., in the gastric or intestinal compartments where drugs are dissolved and absorbed) or provide a method for simultaneously detecting and quantifying multiple sartan and statin drugs and evaluating potential drug-drug interactions under different physiological conditions without having to switch chromatographic parameters.

As current methods do not assess potential drug-drug interactions between sartans and statins or provide a way to simultaneously assess the relative concentrations of a mixture of several sartan and statin drugs in a simple, accurate and reproducible manner, the inventors sought to develop such a method.

As mentioned above patients often need to be treated with both a sartan (antihypertensive drug) and a statin (antilipe-demic drug). The invention provides a simple, accurate and convenient way of assessing potential drug-drug interactions and designing drug regimens and formulations for such patients that minimize over- or under dosing and side-effects of such dual treatment.

BRIEF SUMMARY OF THE INVENTION

The inventors have developed and validated a precise, accurate and economical method for the simultaneous quantification of amounts or concentrations of dissolved losartan and valsartan interacting with statins using high performance liquid chromatography ("HPLC") and UV-visible spectrophotometry. The interactions of different sartan and statin drugs were evaluated using this method. The method of the invention offers many advantages including: (i) a vast number of drugs can be assessed under the same chromatographic conditions; (ii) identification of the peak of drugs can be done accurately by using a simultaneous analytical system; (iii) the method steps are simple and easily applied for regular clinical and pharmaceutical analysis; and/or (iv) the simultaneous method permits assessment of drug-drug interaction. This method helps pharmaceutical manufacturers improve productivity by providing a safe, uncomplicated process that permits drugs to be simultaneously quantified and tested for interaction with other drugs and it shortens testing and production time for drug products. Embodiments of the invention include, but are not limited to:

A method for simultaneously quantifying one or more sartans and one or more statins in a mixture which includes (i) applying the mixture to a RP-HPLC column in a mobile phase comprising acetonitrile and water; and (ii) detecting sartans and statins in said mixture by UV absorption. In a related embodiment, this method is directed to simultaneously quantifying amounts of a dissolved sartan and dissolved statin in a mixture containing at least one sartan and at least one statin by contacting known amounts of least one sartan and at least one statin with one or more solvents to form a mixture, removing undissolved material from the mixture, applying the resulting mixture to a RP-HPLC column in a mobile phase comprising acetonitrile and water in a ratio of no greater than 70:30; quantifying amounts of the at least one sartan and at least one statin dissolved in the mixture by their UV absorption at 220-240 nm; and comparing the UV elution profile of the mixed sartan and statin to a control profile or to a profile of each individual not mixed drug.

RP-HPLC columns are known in the art, for example in various embodiments of the invention a commercially available Ultrasphere® HPLC column may be used, such as an Ultrasphere® HPLC column C18 column or a generic equivalent; see hypertext transfer protocol://_www.macmod.com/pdf/technical-report/036-ColumnComparison-Guide.pdf (last accessed May 21, 2018, incorporated by reference).

Acetonitrile is expensive. In preferred embodiments of the invention, the ratio of acetonitrile:water in the mobile phase is no greater than 70:30 and more preferably about 60:40 in view of expense and technical factors. The pH of the mobile phase may be selected for compatibility with the sample being analyzed, for example, the mobile phase may be adjusted to match a pH of a drug sample dissolved in a synthetic gastric or luminal fluid by use of a buffer or pH adjusting agent.

The invention exemplifies a flow rate of 0.9 mL/min for 6.5 minutes and then amplified to 2.9 mL/min. Depending on the kind of sartan and statin mixtures being assessed, a flow rate and amplified flow rate that provides sample separation and good specificity and sensitivity are used, for example, within the range of 0.7, 0.8, 0.9, 1.0, or 1.1 mL/min for 3, 4, 5, 6, 7, 8, 9 or 10 mins and amplification to >0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 and >3.5 mL/min. Depending on the type of sartan and/or statin being assessed, HPLC may be performed at <5, 5, 10, 15, 20, 25, 30, 35, 37 40, or >40° C. (or any intermediate temperature value or range).

UV detection of sartans or statins may be performed at a UV wavelength between 200-250 nm. Preferably UV detection is performed at 225-235 nm, more preferably at about 230 nm a wavelength selected to efficiently detect a variety of different sartans and statins. These values include all intermediate values and subranges such as 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 and 250. In some embodiments UV detection may be performed at a lambda max value for one or more particular sartans or statins as determined at a particular pH.

A sartan and statin mixture may have an acidic, neutral or alkaline pH. In some embodiments, the pH of the mixture will be the same as or similar to the pH of an acidic gastric compartment, in others neutral, and in still others at an alkaline pH characteristic of a luminal or intestinal compartment. A mixture may have a pH of <1, 1, 1.5, 2, 2.5, 3, 3.5, 4, 4.5, 5, 5.5, 6, 6.5, 7, 7.5, 8, 8.5, 9. 9.5, or >9 or any intermediate value within this range. Suitable buffers are known for providing a mixture at a particular pH and exemplified herein.

Generally, the mixture will contain at least one, two, three, four or more sartans and at least one, two, three, four or more statins so that the method can simultaneously quantify each drug in the mixture. In similar methods a sample containing a single sartan or statin may be provided, for example, as a control or for testing effects of other ingredients such as pharmaceutical excipients or for analysis of a single drug. In other similar methods a mixture of a sartan and/or statin may be made with another non-sartan or non-statin drug such as another class of drug used to treat hypertension (HT), cardiovascular diseases (CVD), hyperlipidemia (HL) or hypercholesterolemia (HC), or comorbid diseases, disorders or conditions, or other diseases such as diabetes, neurodegenerative disease, hormonal imbalance, cancer or an infectious disease. A mixture may also exclude one or more sartans or statins or one or more non-sartan or non-statin drugs including diuretics.

In some embodiments, the mixture will include losartan and at least one of atorvastatin, pravastatin or simvastatin; losartan and at least two of atorvastatin, pravastatin or simvastatin; or losartan and atorvastatin, pravastatin and simvastatin.

In other embodiments, the mixture will include valsartan and at least one of atorvastatin, pravastatin or simvastatin; valsartan and at least two of atorvastatin, pravastatin or simvastatin; or valsartan and atorvastatin, pravastatin and simvastatin.

In other embodiments, the mixture will include losartan and valsartan and at least one of atorvastatin, pravastatin or simvastatin; losartan and valsartan and at least two of atorvastatin, pravastatin or simvastatin; or losartan and valsartan and atorvastatin, pravastatin and simvastatin.

Preferably, a mixture will contain one or more sartans or statins in a linear detection range. For example, as found by the inventors, it may contain at least one of losartan or valsartan and at least one of atorvastatin, pravastatin or simvastatin and wherein losartan has a concentration of 0.0075-0.03 mM (e.g., 0.0075, 0.0150, 0.0225, 0.03); valsartan has a concentration of 0.0045-0.045 mM (e.g., 0.0045, 0.0090, 0.0135, 0.018, 0.0225, 0.027, 0.0315, 0.036, 0.0405, 0.045), atorvastatin has a concentration of 0.005-0.05 mM (e.g., 0.005, 0.01, 0.015, 0.02, 0.025, 0.03, 0.035, 0.04, 0.045, 0.05), pravastatin has a concentration of 0.005-0.05 mM (e.g., 0.005, 0.01, 0.015, 0.02, 0.025, 0.03, 0.035, 0.04, 0.045, 0.05), and simvastatin has a concentration of 0.005-0.005 mM (e.g., 0.005, 0.01, 0.015, 0.02, 0.025, 0.03, 0.035, 0.04, 0.045, 0.05), when present in the mixture. These ranges include all intermediate values and subranges.

The HPLC detection method of the invention may further include performing the method at least two, three, four or more times using the same mixture of sartans and statins, but at two, three, four or more different pHs, and quantifying the relative amounts of soluble sartans and statins in the mixtures at the different pHs. This provides information regarding mixed drug dissolution and availability at under different physiological conditions.

These different pHs may range from a pH of <1, 1, 1.5, 2, 2.5, 3, 3.5, 4, 4.5, 5, 5.5, 6, 6.5, 7, 7.5, 8, 8.5, 9. 9.5, or >9 or any intermediate value within this range, for example, at pH 1, 4, 7.4 and 9. Such a mixture may be produced by dissolving, suspending or otherwise admixing one or more isolated or pure sartans and statins in a buffer at a desired pH for >0, 0.125, 0.25, 0.5, 0.75, 1, 2, 3, 4, or >4 hours (or any intermediate period of time). Alternatively, the mixture may be produced using a sartan and statin as manufactured prior to tableting, encapsulation or production of other individual dosage forms (e.g., a bulk proprietary or generic drug). In other embodiments, the mixture will be produced from tablets or individual dosage forms including their excipients, for example, by dissolving a tablet of a prescription sartan or statin in a buffer of choice. In still other embodiments, the sartan and/or statin may be dissolved under conditions similar to those in the stomach or intestines, for example, in the presence of one or more foods, alcohol, antacids, non-sartan or non-statin drugs, or microorganisms found in the gastrointestinal tract.

A pH value may be selected based on patient-specific characteristics such as a patient's own gastric or luminal pH, a fasting pH, a postprandial pH at 0, 0.25, 0.5, 0.75, 1, 1.5, 2, 2.5, 3, 3.5 or 4 hours after a meal, post-exercise gastric or luminal pH, or on gastric or luminal pH after taking antacids, reflux medicines, or other drugs, vitamins or foods affecting physiological pH. It may also take into account surgical procedures such as Roux-en-Y gastric bypass or other gastric bypass, or other bariatric surgery or modifications (stapling, banding, balloons) or other GI surgeries or conditions (e.g., gall bladder removal, liver and gall bladder status, Crohn's disease, reflux, obesity). Such a method may also further include selecting a drug or drug regimen comprising administering at least one sartan and at least one statin that provides safe and effective amounts of the at least one sartan and at least one statin to a subject in need of treatment with a sartan and a statin.

The inventors have developed a method that can assess the role of pH in prevailing drug interactions or for new as yet unidentified interactions. The assessment of pH as a pharmacological or pharmacokinetic factor helps decide the physiological site of the interaction and hence gives a clear indication of where the two drugs should not be together. The simulated gastric juice and simulated intestinal juice represent two physiological sites (stomach before taking food and intestine, respectively). One of the sites has acidic pH while the other one has an alkaline pH. For example, both losartan and valsartan absorb at 206 nm approx., owing to the π-π* at the tetrazole ring and considering that ARBs possess number of binding sites and their electron cloud is delocalized over a large area, drug interaction may occur at acidic or alkaline pH. So a thorough monitoring of interactions at most probable physiological pH is important, in order to preserve the efficacy of a combined sartan and statin therapy.

In other embodiments, this method may further include selecting a drug formulation for at least one sartan and at least one statin that provides safe and effective amounts of the at least one sartan and at least one statin to a subject in need of treatment with a sartan and a statin. In some embodiments a drug formulation that releases the at least one sartan in an acidic gastric compartment and the at least one statin in an alkaline luminal compartment, or vice versa. For example, a sartan or statin may be formulated with an enteric coating that dissolves at an alkaline pH to avoid release in the stomach and permit subsequent release in the intestines. In other formulations for release in the stomach, an enteric coating is not provided. In other embodiments, a drug formulation is designed or formulated to release both the sartan and statin in an acidic gastric compartment or both in an alkaline luminal compartment. Alternatively, some sartans and some statins may be formulated for release in the stomach and others for release in the intestines.

BRIEF DESCRIPTION OF THE SEVERAL VIEWS OF THE DRAWING(S)

A more complete appreciation of the invention and many of the attendant advantages thereof will be readily obtained as the same becomes better understood by reference to the following detailed description when considered in connection with the accompanying drawings, wherein:

FIG. 1: Shows a chromatogram and separation of antihypertensive drugs losartan and valsartan and three antilipidemic statins: atorvastatin, pravastatin and simvastatin.

Figure 2:
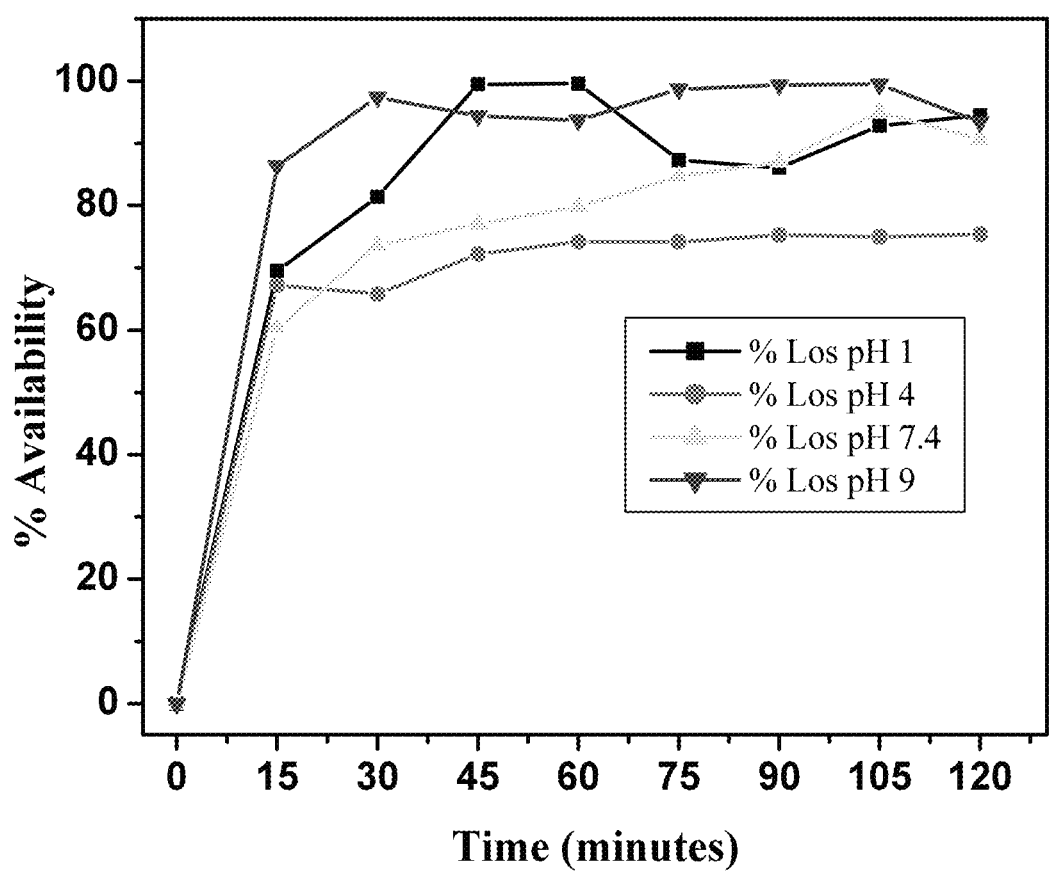

FIG. 2: In vitro release of Losartan in various media at 206 nm (Losartan added=0.118 mM, % Los=% released Losartan).

Figure 3:
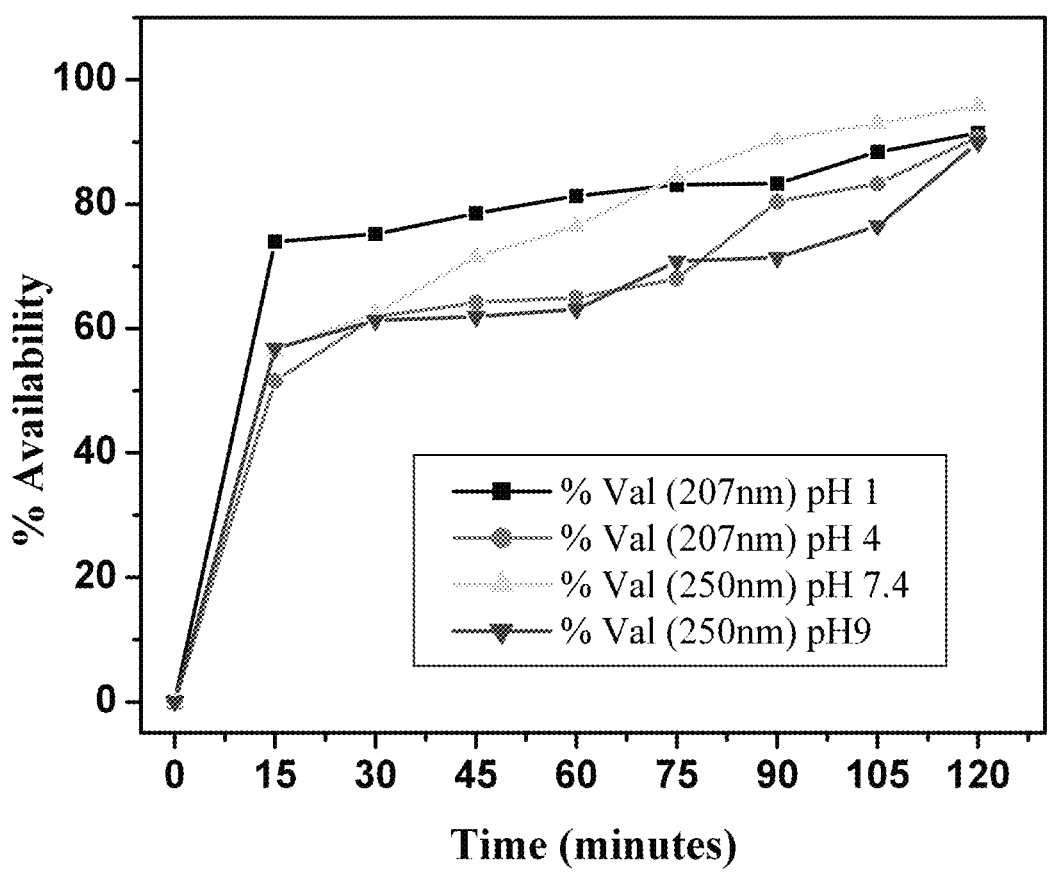

FIG. 3: In vitro release of Valsartan in various media (Valsartan added=0.184 mM, % Val=% released Valsartan).

Figure 4:
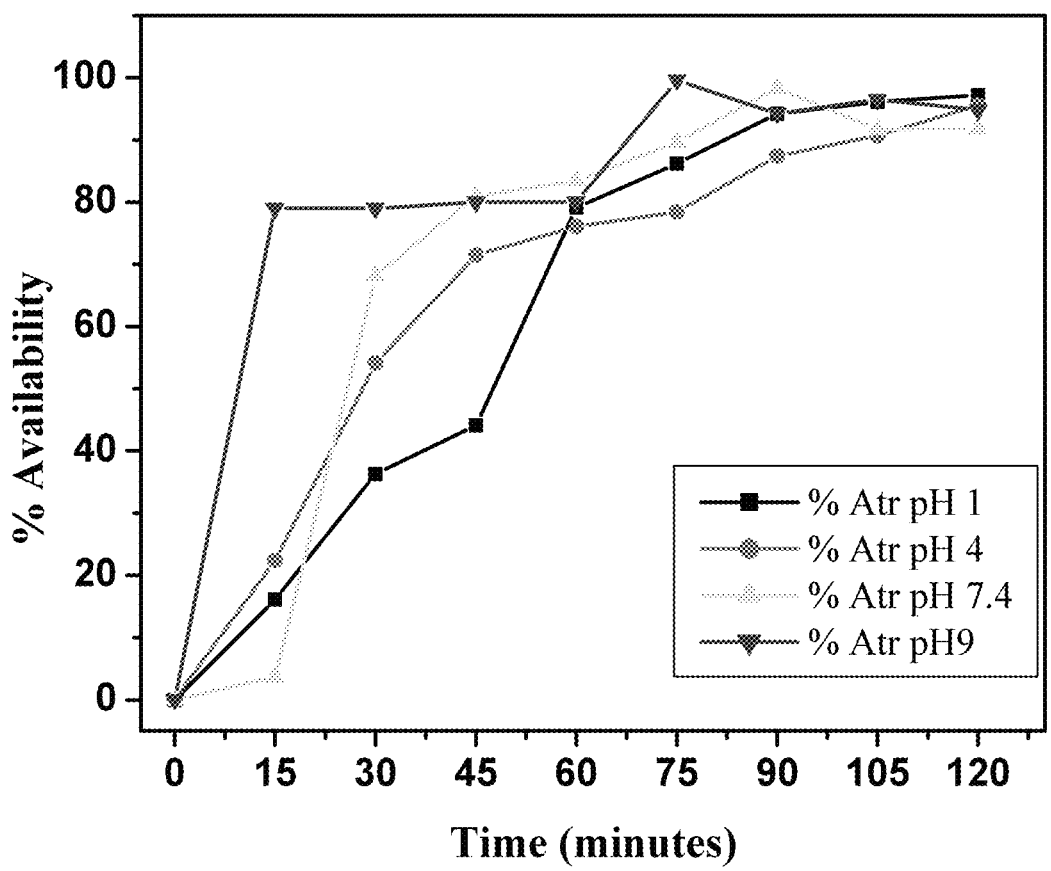

FIG. 4: In vitro availability of atorvastatin in various media at 241 nm (Atorvastatin added=1.7 mM, % Atr=% released atorvastatin).

Figure 5:
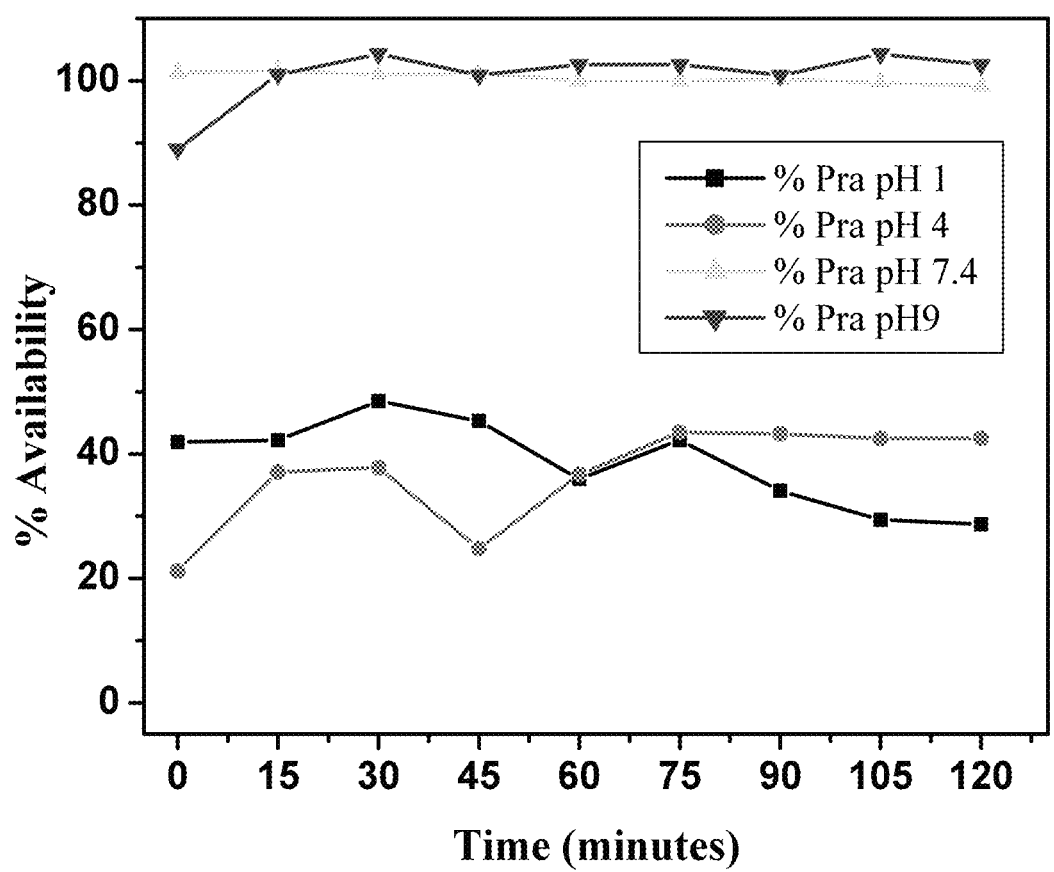

FIG. 5: In vitro release of pravastatin in various media at 225 nm (Pravastatin added=4.71 mM, % Pra=% released pravastatin).

Figure 6:
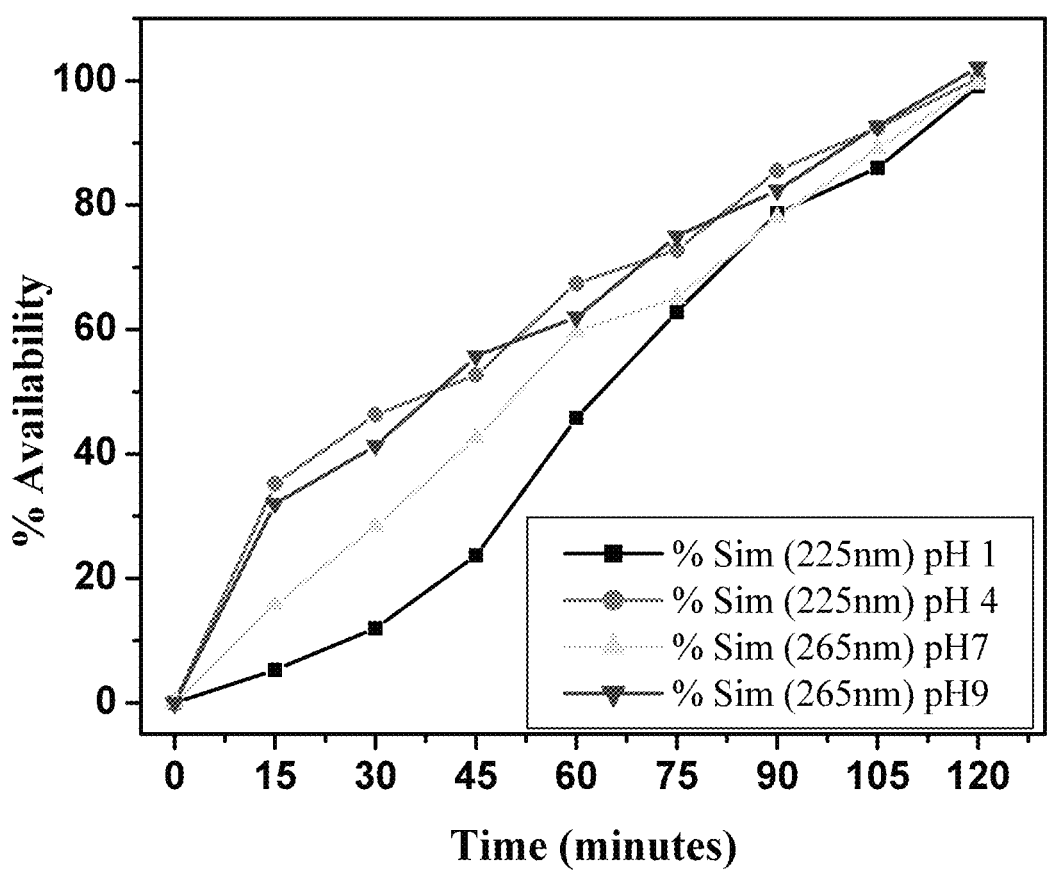

FIG. 6: In vitro release of simvastatin in various medium (Simvastatin added=4.7 mM, % Sim=% released simvastatin).

Figure 7:
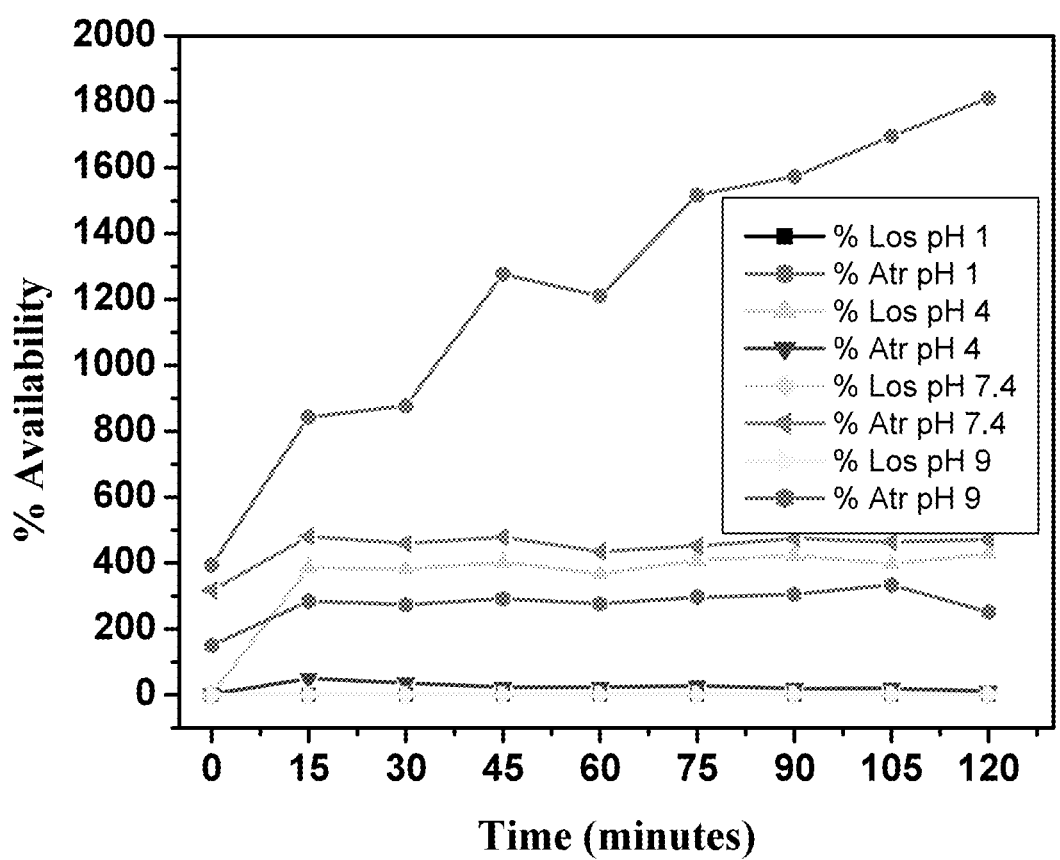

FIG. 7: In vitro release of losartan and atorvastatin after interaction studied by UV-Visible spectrophotometer (%=% released; Los=Losartan; Atr=Atorvastatin).

Figure 8:
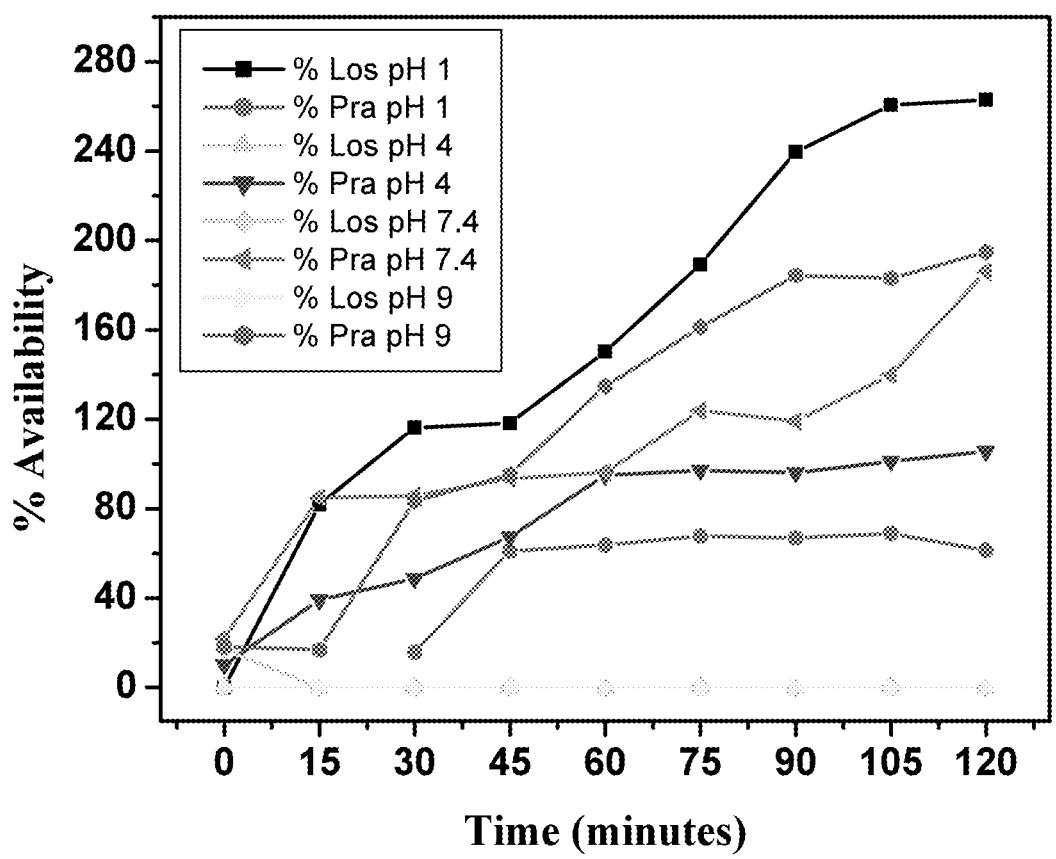

FIG. 8: In vitro release of losartan and pravastatin after interaction studied by UV-Visible spectrophotometer (%=% released; Los=Losartan; Pra=Pravastatin).

Figure 9:
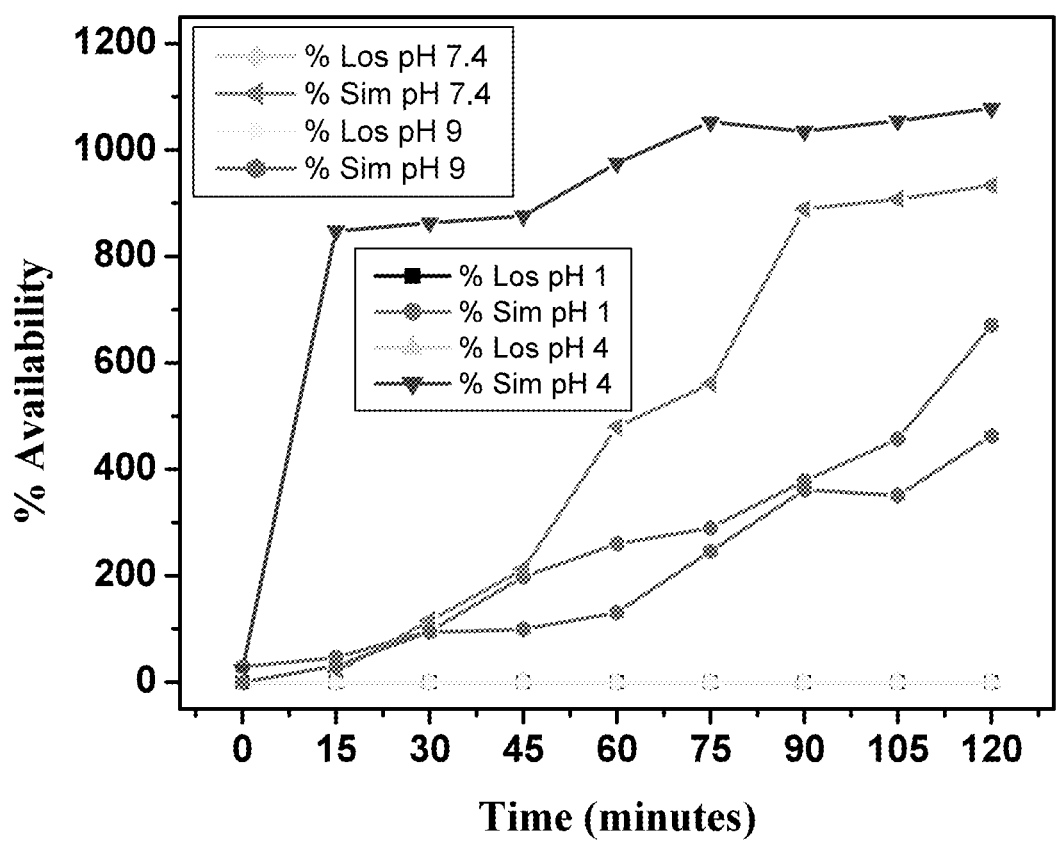

FIG. 9: In vitro release of losartan and simvastatin after interaction studied by UV-Visible spectrophotometer (%=% released; Los=Losartan; Sim=Simvastatin).

Figure 10:
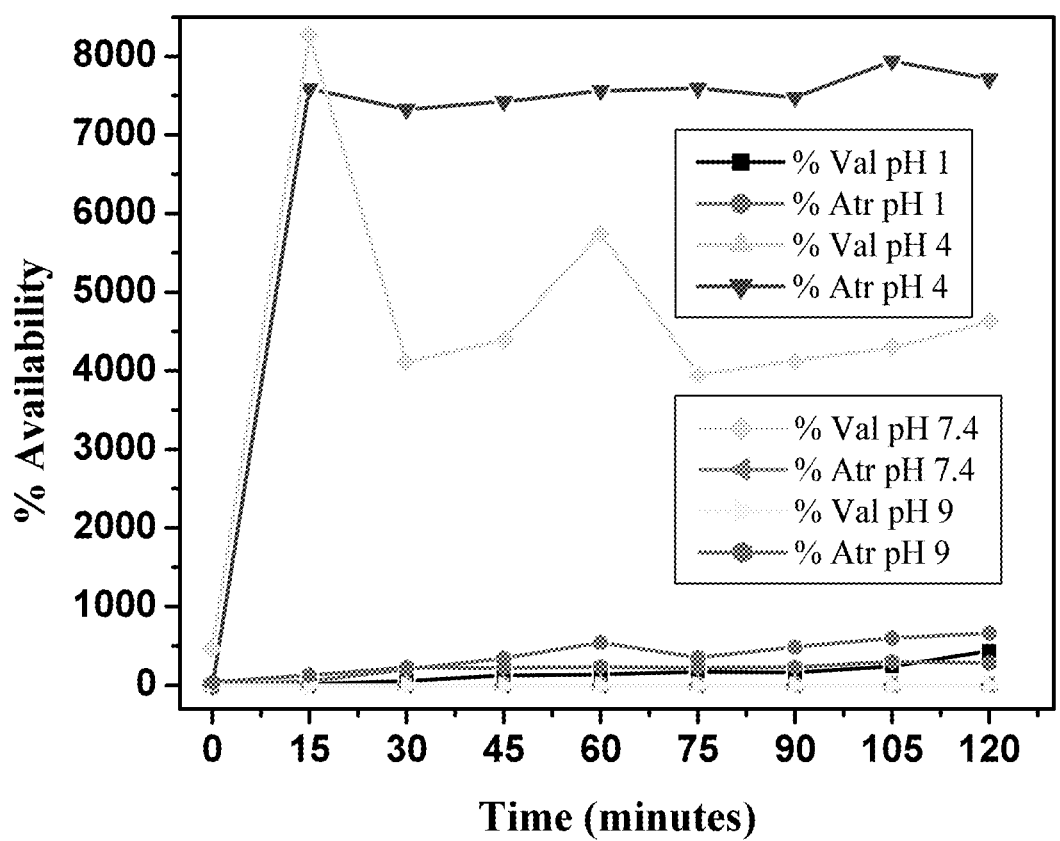

FIG. 10: In vitro release of valsartan and atorvastatin after interaction studied by UV-Visible spectrophotometer (%=% released; Val=Valsartan; Atr=Atorvastatin).

Figure 11:
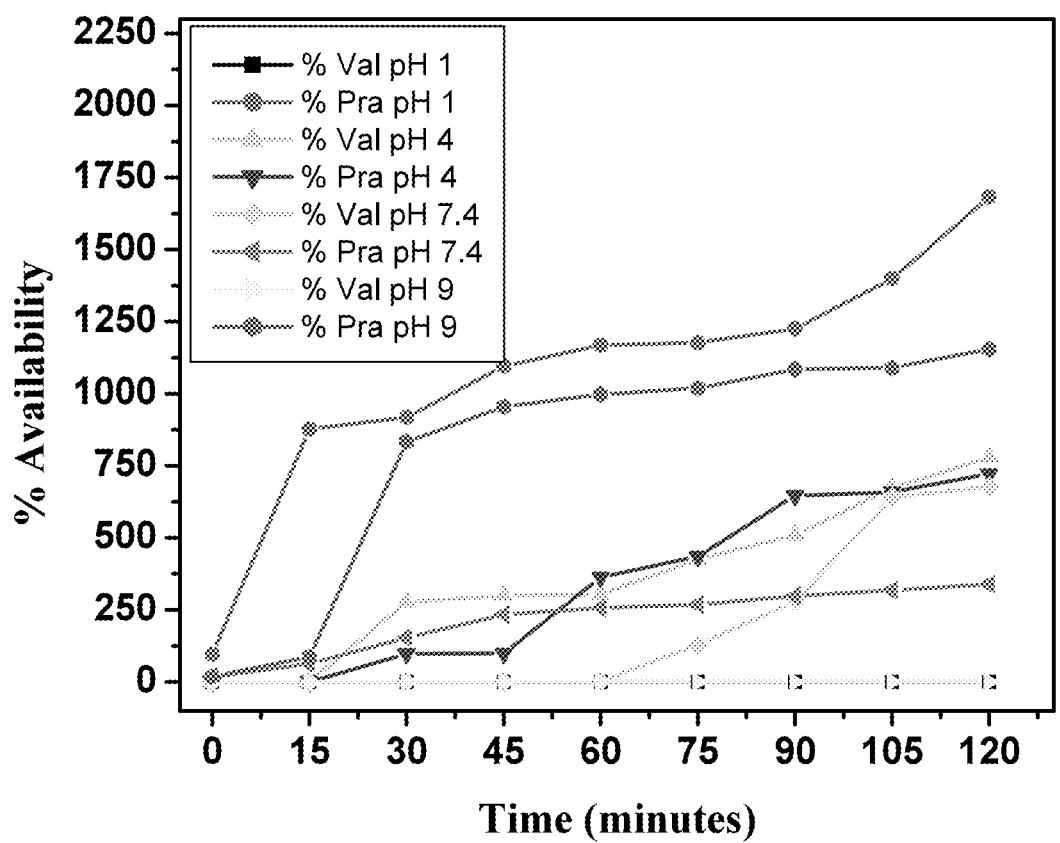

FIG. 11: In vitro release of valsartan and pravastatin after interaction studied by UV-Visible spectrophotometer (%=% released; Val=Valsartan; Pra=Pravastatin).

Figure 12:
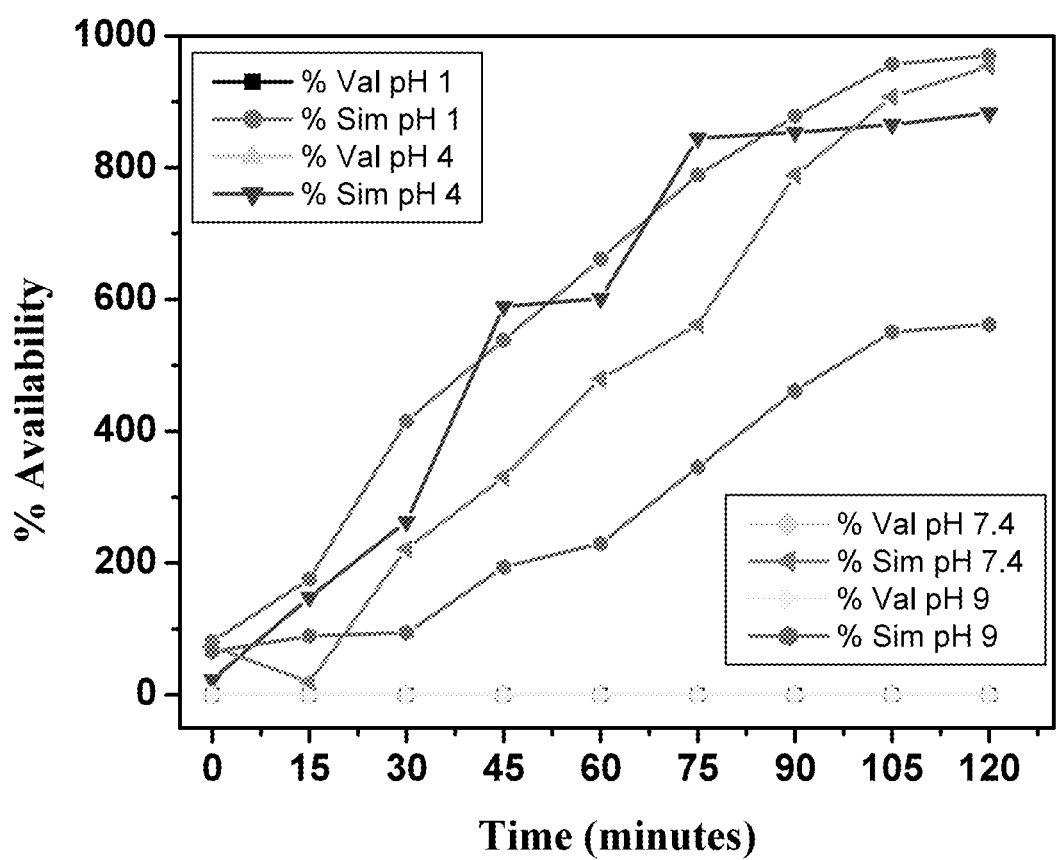

FIG. 12: In vitro release of valsartan and simvastatin after interaction studied by UV-Visible spectrophotometer (%=% released; Val=Valsartan; Sim=Simvastatin).

Figure 13:
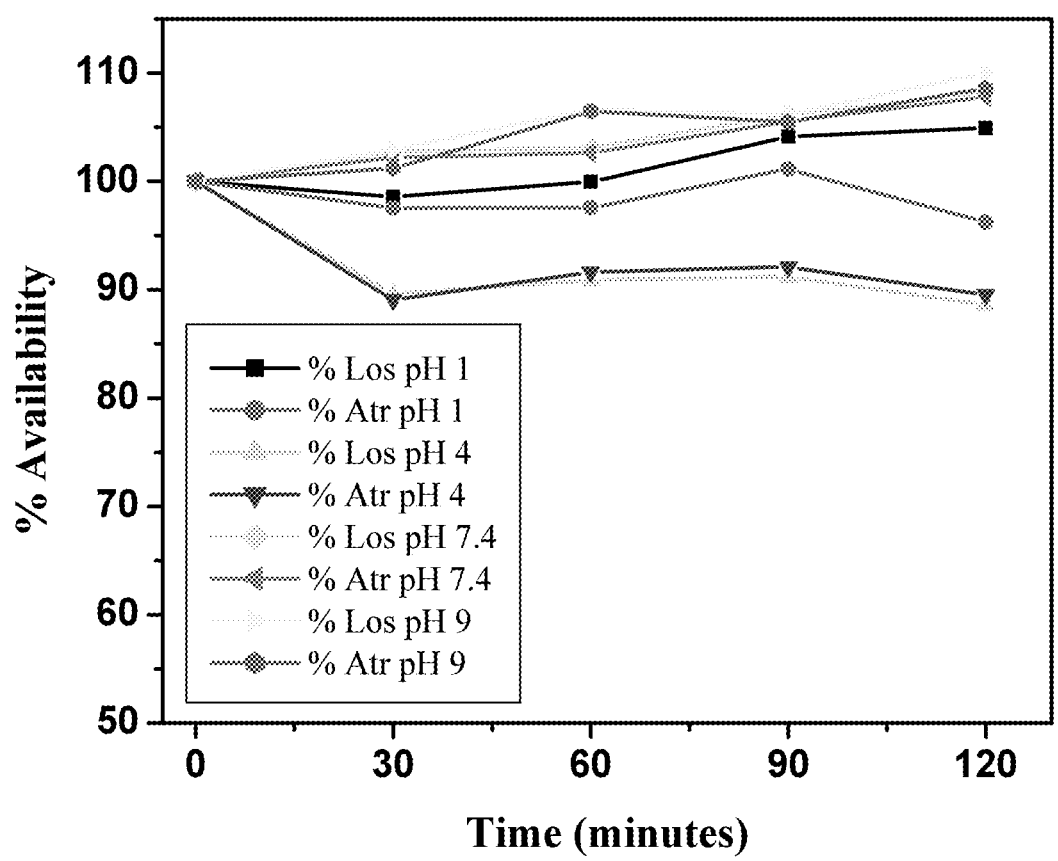

FIG. 13: Availability of losartan and atorvastatin after interaction studied by RP-HPLC.

Figure 14:
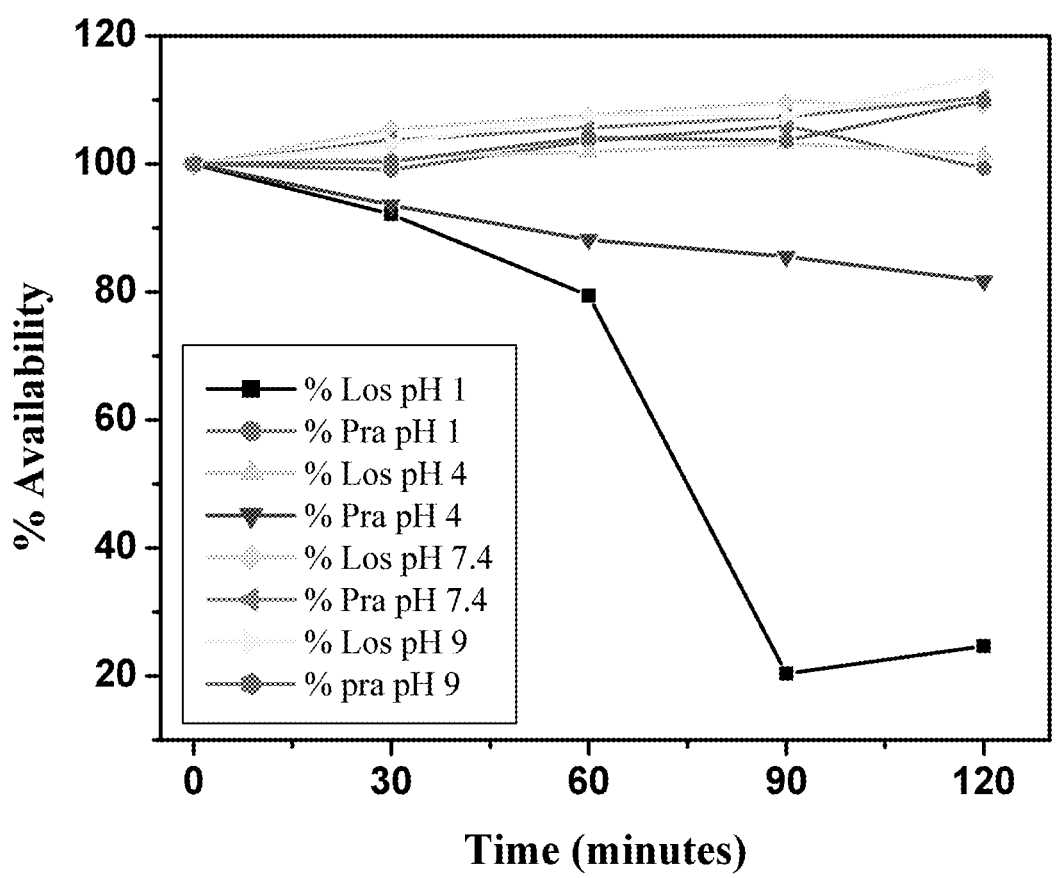

FIG. 14: Availability of losartan and pravastatin after interaction studied by RP-HPLC.

Figure 15:
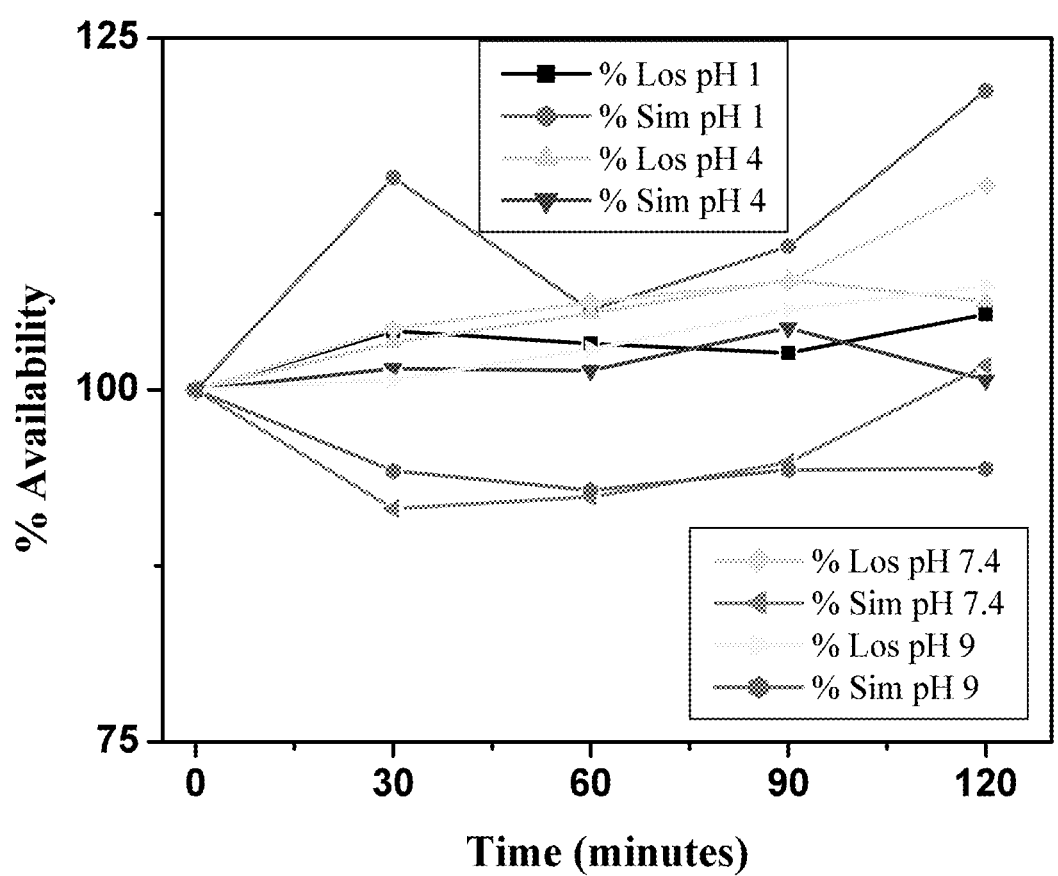

FIG. 15: Availability of losartan and simvastatin after interaction studied by RP-HPLC.

Figure 16:
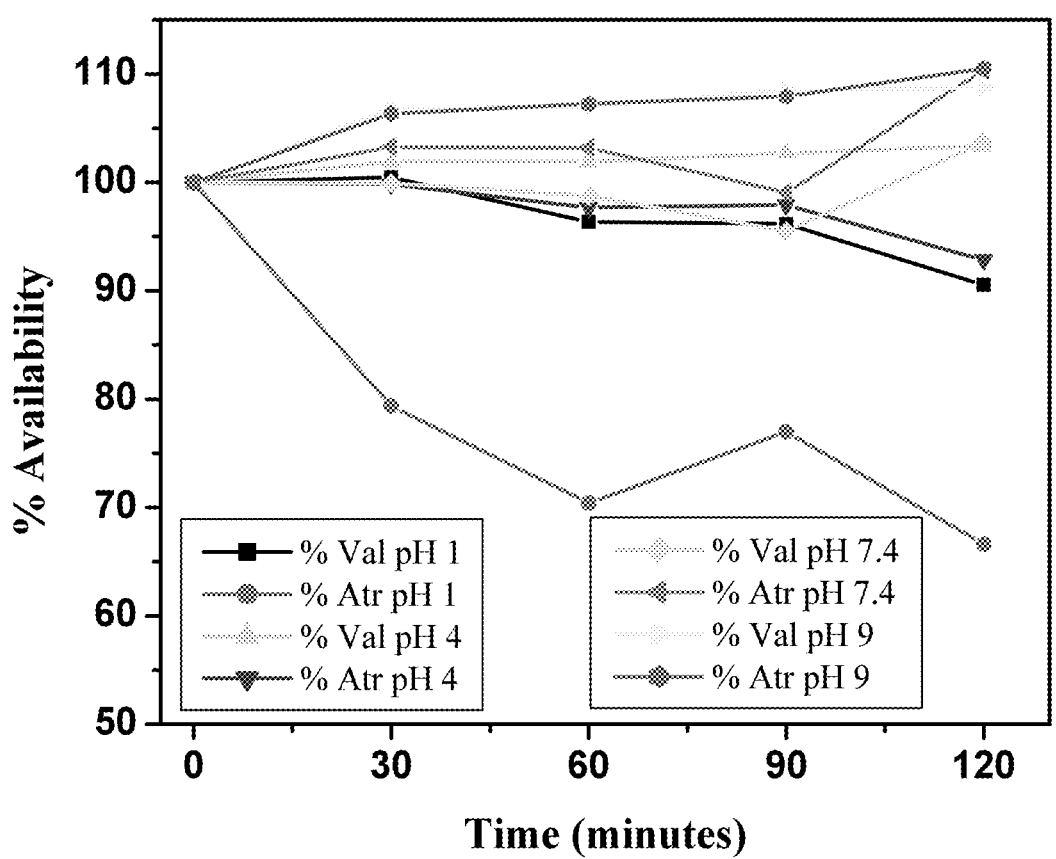

FIG. 16: Availability of valsartan and atorvastatin after interaction studied by RP-HPLC.

Figure 17:
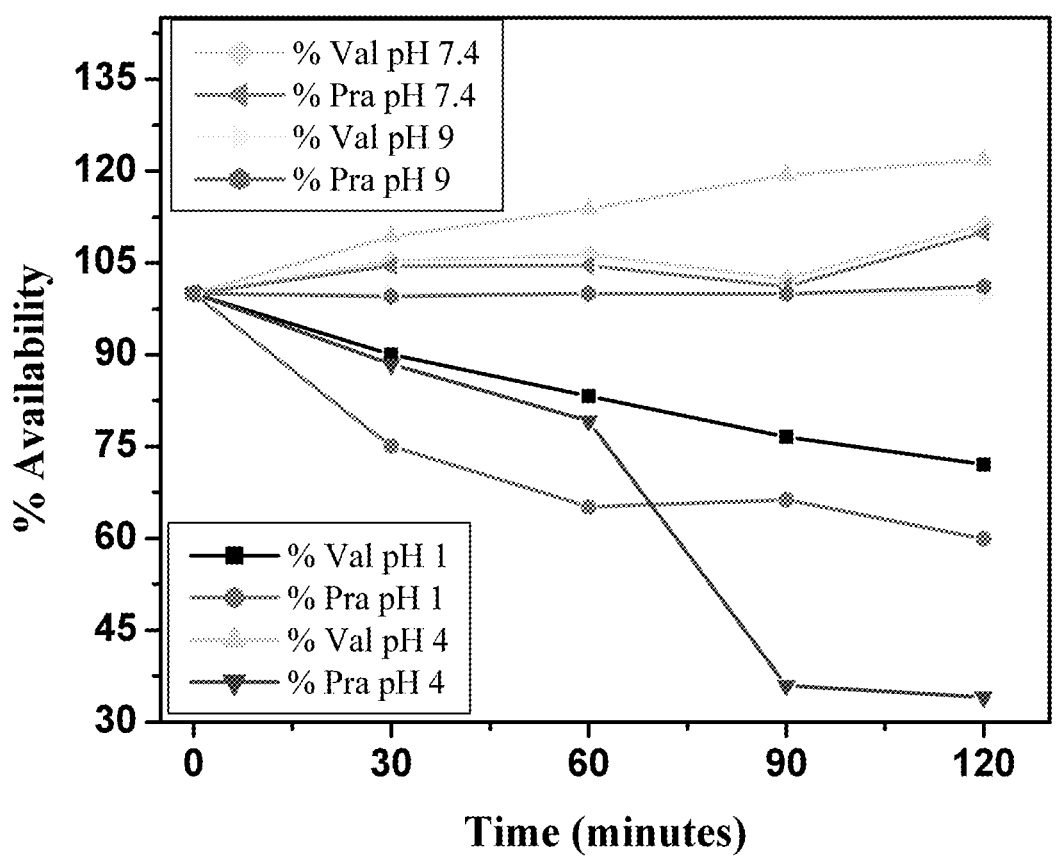

FIG. 17: Availability of valsartan and pravastatin after interaction studied by RP-HPLC.

Figure 18:
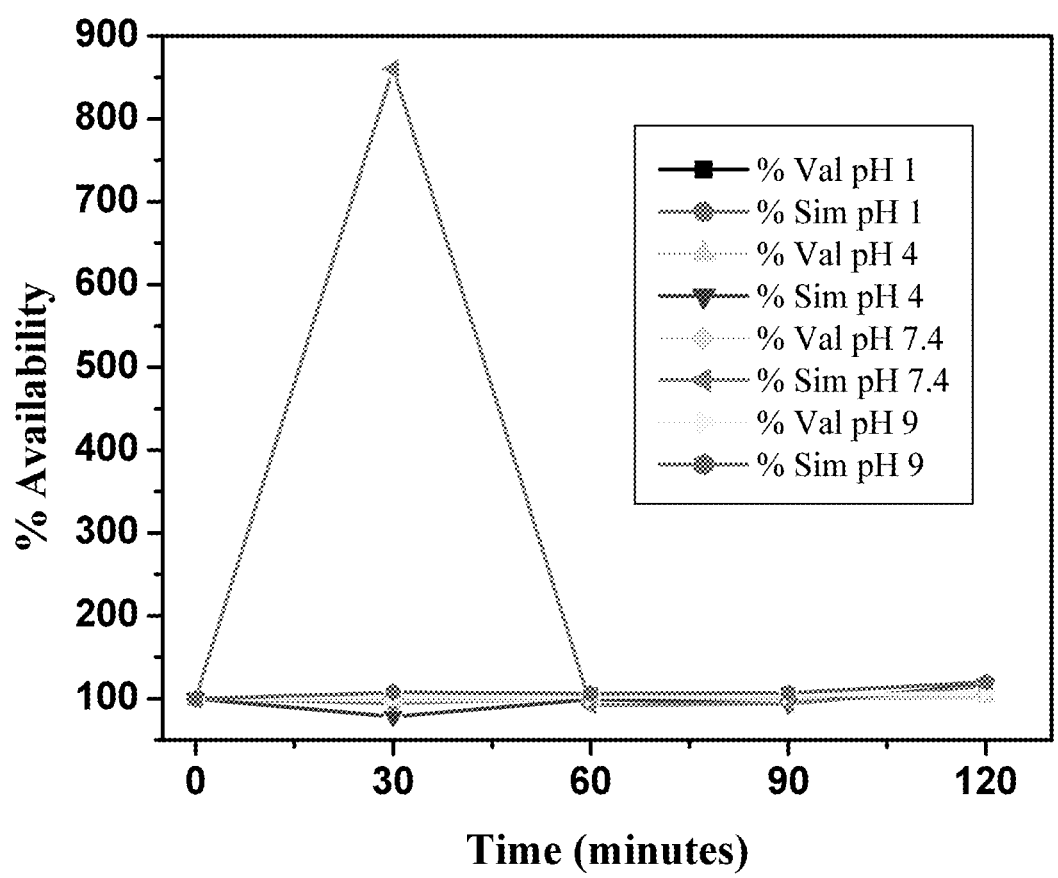

FIG. 18: Availability of valsartan and simvastatin after interaction studied by RP-HPLC.

DETAILED DESCRIPTION OF THE INVENTION

Drug-Drug Interaction Studies of Losartan and Valsartan with three Statins in Bulk Drug and Pharmaceuticals. As disclosed herein, the inventors have developed a quantitative method for simultaneous liquid chromatography and analysis of mixtures of sartan and statin drugs by UV spectroscopy. This method is applied to mixtures of such as losartan and valsartan and one or more statins such as atorvastatin, pravastatin and simvastatin. It involves in vitro analysis and detection of interactions (or non-interactions) of a mixture of at least two drugs by performing liquid chromatography on the mixture and detecting eluted components by their UV absorbance. The chromatographic pattern of the mixed drugs can be compared to a positive or negative control profile or to a chromatographic pattern of each individual not mixed drug.

Advantageously, the method is directed to analyzing and detecting interactions between ARBs (e.g., angiotensin-II receptor blocker, angiotensin II receptor antagonist, AT1 receptor antagonist or sartan), and statins (e.g., HMG-CoA reductase inhibitors) and provides a single method for the detection as well as quantification of multiple drugs.

As one example, the method can simultaneously evaluate a combination of two ARBs and three statins. This allows the user, such as a pharmaceutical company, generic drug manufacturer, R&D department, clinical lab or regulatory authority such as the Food and Drug Administration, to test these five drugs using one single method. Development of a single, simultaneous method provides easy, reliable and fast detection and quantification for these five drugs either alone or in combination, using same chromatographic conditions without having to switch chromatographic parameters.

In alternate embodiments, the method can be used for the detection of only sartans or only statins or a single sartan or statin or a combination of a single sartan or statin with another drug or excipient. This method has been validated for testing of bulk drugs as well as dosage forms and can confirm that excipients used in dosage forms do not interfere with the retention time of a tested drugs.

The method of the invention provides a convenient way to identify drug-drug or drug-excipient interactions and determine at which pH and under which other conditions such interactions occur. It permits a determination of a safe and efficacious drug regimen for a patient suffering from a condition requiring cotreatment with both a sartan and a statin.

Sartans or Angiotensin II receptor antagonists ("ARBs") are a group of pharmaceuticals that modulate the renin-angiotensin-aldosterone system. Their main uses are in the treatment of hypertension (high blood pressure), diabetic nephropathy (kidney damage due to diabetes) and congestive heart failure. Sartans may also be used to treat reperfusion arrhythmias, post-traumatic stress disorder, and may exhibit positive effects on longevity. Sartans include those in bulk form, including proprietary statins and generic statins, and those formulated for administration, such as a sartan in combination with one or more excipients or a sartan in combination with a statin or other medication. Sartans include azilsartan (Edarbi®), candesartan, eprosartan, EXP-3174, fimasartan, losartan, irbesarten, olmesartan, saprisartan, telmisartan and valsartan. Sartans include those in bulk form, including proprietary and generic sartans, isolated or pure sartans, and those formulated for administration such as tablets, capsules, etc. of known dosage which may include excipients or other active ingredients.

A sartan can have a biological half-life ranging from less than 6 to more than 24 hours, such as <6, 6, 7, 8, 9, 10, 11, 12, 13, 14, 15, 16, 17, 18, 19, 20, 21, 22, 23, 24 and >24 hrs. Relative affinity of a sartan from AT1 vs AT2 may range from less than 1,000-fold to greater than 30,000-fold, for example, <1,000, 1,000, 2,000, 3,000, 4,000, 5,000, 8,500, 10,000, 12,500, 15,000, 20,000, 25,000, 30,000 or >30,000-fold as well as any intermediate value or subrange within this range.

Sartan side-effects include dizziness, headache, and/or hyperkalemia as well as first dose orthostatic hypotension, rash, diarrhea, dyspepsia, abnormal liver function, muscle cramp, myalgia, back pain, insomnia, decreased hemoglobin levels, angioedema, renal impairment, pharyngitis, and/or nasal congestion.

The method of the invention, by assessing drug interactions with other sartans or statins and/or excipients, can help reduce sartan side-effects through selection of a safe and effective drug regimen, dosage, drug combinations, or suitable excipients.

Statins, also known as HMG-CoA reductase inhibitors, are a class of lipid-lowering medications. Statins have been found to reduce cardiovascular disease (CVD) and mortality in those who are at high risk of cardiovascular disease such as those having elevated cholesterol levels, high blood pressure, obesity, a family history of heart attacks, those more than 40, 45, 50, 60, 65, 70, 75, 80, 85, 90, 95 years old, diabetics (including Type 1 and Type 2 diabetes), those having high blood pressure or the obese (e.g., BMI greater than 18.5 to 24.9, 25 to 29.9, 30, or 40), and those suffering from the complications of atherosclerosis including angina, heart attacks, plaques, stroke, intermittent claudication, and death.

Statins include atorvastatin (Lipitor), fluvastatin (Lescol, Lexcol XL), lovastatin (Mevacor, Altoprev), pravastatin (Pravachol), pitavastatin (Livalo), rosuvastatin (Cretor), and simvastatin (Zocor) as well as various statin combinations, such as lovastatin with niacin or simvastatin with niacin. Statins include those in bulk form, including proprietary statins and generic statins in isolated or pure form, or as compounded with other excipients or active ingredients, and those formulated for administration such as unit dosage forms like tablets or capsules.

Statin side-effects include headache, nausea, vomiting, constipation, diarrhea, rash, weakness, and muscle pain. Other side-effects may include liver failure and rhabdomyolysis (injury or death of muscle tissue), memory loss, forgetfulness, amnesia, confusion, and memory impairment.

The method of the invention by assessing drug interactions with other statins or sartans and/or excipients can help reduce statin side-effects through selection of safe and effective drug regimen, dosing, drug combinations or suitable excipients.

Diuretics are drugs that increase urine output and often used to reduce high blood pressure. They include thiazide diuretics such as bendroflumethiazide, chlorothiazide, chlorthalidone, hydrochlorothiazide, indapamide, and metolazone; loop diuretics such as ethacryinic acid, bumetanide, furosemide or torsemide; potassium-sparing diuretics such as amiloride, eplerenon, spironolactone, and triamterene; and carbonic anhydrase inhibitors such as acetazolamide. The method of the invention may be used to quantify or assess interactions of one or more diuretics with a sartan, statin, or sartan and statin under different physiological conditions. Some pharmaceutical products, such as Edarbichlor® contain both a sartan and a diuretic. The method of the invention may be used to assess drugs like Edarbichlor® when coadministered with a statin.

Simulated gastric fluid (SGF) or gastric juice is a synthetic form of the gastric fluid in the stomach. This fluid will show the effect of the gastric juice in the stomach on a particular drug in the stomach and help assess drug interactions occurring in the stomach.

Mixtures of sartans and statins can be suspended or dissolved in simulated gastric fluid or juice, solid or insoluble materials removed for example by filtration or centrifugation and samples of the soluble phase containing the sartan and/or statins analyzed.

Methods and components for SGF include those described by hypertext transfer protocol secure://_bioscience-education.blogspot.com/2014/06/preparation-of-simulated-gastric-fluid.html (incorporated by reference, last accessed May 16, 2018) and may have a pH, ionic components, protein components or one or more other components of human gastric juices described by hypertext transfer protocol secure://_www.ncbi.nlm.nih.gov/pmc/articles/PMC3339592/(incorporated by reference, last accessed May 16, 2018). Other simulated gastric or intestinal fluids include those described and incorporated by reference to Jantratid, et al., Dissolution Technologies (AUGUST 2009) or those that are commercially available. Examples of simulated gastric fluids include 0.1N HCl at pH 1.0-1.2 and those having 0.1047-0.1058 M NaCl, 0.7068-0.07139 M HCl, and a pH of 1.1 to 1.3 at 25° C.

Mixtures containing 1, 2, 3, 4, 5 or more sartans and 1, 2, 3, 4, 5 or more statins may be assessed using the HPLC method and UV absorbance steps of the invention. Such mixtures may be suspended or dissolved in simulated gastric fluid, solid or insoluble materials removed for example by filtration or centrifugation and samples of the soluble phase containing the sartan and/or statins analyzed.

Simulated intestinal fluid or juice is a synthetic form of fluids in the intestine. These include those described at hypertext transfer protocol://_www.dissolutiontech.com/DTresour/200405Articles/DT200405_A01.pdf (last accessed May 16, 2018, incorporated by reference) as well as phosphate buffer at pH 6.8, the Simulated Intestinal Fluid (SIFsp) described in *The 26$^{th}$ United States Pharmacopeia* (USP 26) as an 0.05 M buffer solution containing potassium dihydrogenphosphate; and Phosphate Standard Buffer pH 6.8 TS described in Volume 1 of *The International Pharmacopoeia*, Third Edition, (IntPh 3) as a mixture of 0.025 M potassium dihydrogen phosphate buffer solution and 0.025 M di-sodium hydrogen phosphate buffer solution.

Mixtures containing 1, 2, 3, 4, 5 or more sartans and 1, 2, 3, 4, 5 or more statins may be assessed using the HPLC method and UV absorbance steps of the invention. Such mixtures may be suspended or dissolved in artificial intestinal fluid, solid or insoluble materials removed for example by filtration or centrifugation and samples of the soluble phase containing the sartan and/or statins analyzed.

Buffers are well known in the chemical and pharmaceutical arts and include those described by hypertext transfer protocol secure://_en.wikipedia.org/wikiBuffer_solution (last accessed May 18, 2018, incorporated by reference. A buffer may provide a pH of <1, 1, 1.5, 2, 2.5, 3, 3.5, 4, 4.5, 5, 5.5, 6, 6.5, 7, 7.5, 8, 8.5, 9. 9.5, or >9 or any intermediate value within this range. Buffers include hydrochloric acid buffer, acid phthalate buffer, neutralized phthalate buffer, phosphate buffer, alkaline borate buffer, acetate buffer at pH 2.8, 3.4, 3.5, 3.7, 4.0, 4.4, 5.0, 5.5, or 6.0, acetate-edetate buffer, acetic acid-ammonium acetate buffer, ammonia buffer, barbitone buffer, HEPES buffer, carbonate buffer, citro-phosphate buffer, and TRIS buffer. Specific buffers and buffer formulates are incorporated by reference to or hypertext transfer protocol secure://_www.pharmaguideline.com/2010/09/preparation-of-buffer-solutions.html (last accessed May 21, 2018).

Liquid chromatography ("LC") is a technique for the separation of a liquid mixture. The mixture is dissolved in a fluid called the mobile phase, which carries it through a structure holding another material called the stationary phase. The various constituents of the mixture travel at different speeds causing them to separate. The separation is based on differential partitioning between the mobile and stationary phases. Subtle differences in a compound's partition coefficient result in differential retention on the stationary phase and thus affect the separation.

High-performance liquid chromatography ("HPLC") is a technique used to separate, identify, and quantify each component in a mixture. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column.

Reversed phase HPLC ("RP-HPLC") has a non-polar stationary phase and an aqueous, moderately polar mobile phase. One common stationary phase is silica which has been surface-modified with $RMe_2SiCl$, where R is a straight chain alkyl group such as $C_{18}H_{37}$ or $C_8H_{17}$. With such stationary phases, retention time is longer for molecules which are less polar, while polar molecules elute more readily.

Linearity refers to the response of a detector. A detector is linear if the output of a detector is given by the product of a constant and the solute concentration (or, for a mass sensitive detector, the mass of solute passing though it per unit time). If a detector is declared to be linear, the linearity is usually limited to a specific concentration range (or range of mass of solute passing though it per unit time).

Liberation is the process of release of a drug from a pharmaceutical preparation. When two drugs such as a sartan and a statin, are administered into the same biological compartment the combination may inhibit the liberation or one or both of the drugs.

Absorption is the movement of a drug from the site of administration, such as from the stomach or intestine, to the bloodstream.

Bioavailability is a subcategory of absorption and is the fraction of an administered dose of unchanged drug that reaches the systemic circulation, one of the principal pharmacokinetic properties of drugs. By definition, when a medication is administered intravenously, its bioavailability is 100%. However, when a medication is administered via other routes such as orally, its bioavailability generally decreases due to incomplete absorption and first-pass metabolism and can vary from patient to patient. Bioavailability is one of the essential tools in pharmacokinetics, as bioavailability must be considered when calculating dosages for non-intravenous routes of administration.

The inventors have developed an analytical UV method useful for detecting concentrations of sartans or statins in a sample liberated under different physiological conditions such as at pH 1, 4, 7 and 9 and an HPLC method that simultaneously detects concentrations of individual sartans and statins in a mixture of containing a mixture of multiple sartans and statins.

EXAMPLE

Quantitative Analysis of Mixture of Two Sartans (Losartan and Valsartan) and Three Statins (Atorvastatin, Pravastatin and Simvastatin)

The method according to the invention provided a simultaneous quantitative analysis of the two antihypertensive sartan drugs and three antilipidemic statin drugs and permitted precise monitoring of drug-drug interactions between or among these drugs and their dissolution and liberation over a range of different physiological pHs.

HPLC was performed on a mixture of the two sartans and three statins using acetonitrile:$H_2O$ (60:40 v/v, pH 2.9), kept at a flow rate of 0.9 mL/min for 6.5 minutes and then amplified to 2.9 mL/min, as mobile phase. The inventors selected instrumental calibrations that allowed the solvent to flow at the rate of 0.9 ml/min until 6.5 minutes to facilitate elution of four drugs, in the order of Pravastatin, Losartan, Valsartan & Atorvastatin. Subsequently, the flow rate was increased to 2.9 ml/min (changed at 6.5-7 mins) for the elution of simvastatin at about 10 minutes. The use of pH 2.9 (with Phosphoric acid) ensured better and sharp peaks. The selection of wavelength was made by finding UV cutoff points of all 5 drugs to select a wavelength at which all/each drug(s) absorb.

UV detection at 230 nm was conducted for the monitoring of analytes, using gradient elution. Linearity was achieved (05-100 µg/mL, correlation coefficients>0.999) and the method was effectively developed as well as validated for the analysis of all the analytes in pharmaceutical dosage formulations.

The chromatogram in in the FIG shows the separation of antihypertensive drugs (losartan and valsartan) and three antilipidemic statins (atorvastatin, pravastatin and simvastatin) resolved using this method. As shown the inventors developed a method where sartan and statin drugs were eluted with good resolution between the peaks and a short run time allowing a user to make both cost effective and time saving experiments. As shown herein, the method allowed the detection and quantification of five drugs, where four of the drugs were eluted within 6 minutes, while the fifth drug, simvastatin, was eluted near a 10 minute mark. The method had a total run time of approximately 11.5 minutes, thus providing a fast and more economical method than conventional methods requiring longer runtimes. A reduction in run time conserves the amount of costly acetonitrile used.

Materials and Reagents. Acetonitrile and methanol were of HPLC grade (TEDIA®, USA), ammonia solution 26%, HCl, orthophosphoric acid (85%) (Merck Damstabt, Germany), KCl, potassium dihydrogen orthophosphate, disodium hydrogen orthophosphate, NaCl and ammonium chloride (Sigma Aldrich, Germany) were used. Losartan (LOS), Valsartan (VAL), Pravastatin (PRA), Atorvastatin (ATR) and Simvastatin (SIM) reference standards were purchased from Sigma Aldrich. All dosage formulations were purchased from a local market. De-ionized water (double distilled) was used in all experiments.

Instruments and chromatographic conditions. UV-Visible double beam spectrophotometer (Shimadzu 1601 along with UVPC version 3.9 software), HPLC systems consisting of (pump Shimadzu LC-10 AT VP), (SPD-10 AV VP UV-Visible detector), CBM-102 Bus Module integrator and column Beckman ODS-DABS, Ultrasphere™ $C_{18}$ (5µ, 25 cm×4.6 mm) were used.

Acetonitrile:$H_2O$ (60:40 v/v, pH 2.9) kept at a flow rate of 0.9 mL/min for 6.5 minutes and then amplified to 2.9 mL/min, was used as mobile phase. UV detection was performed at 230 nm for monitoring the analytes, using gradient elution (Table 1).

TABLE 1

Separation conditions for antihypertensive drugs and antilipidemic agents

| Analytes | Mobile phase | Flow rate mLmin$^{-1}$ | λ nm | Linearity µgmL$^{-1}$ | Diluents |
|---|---|---|---|---|---|
| Los + Val + Atr + Pra + Sim | ACN:$H_2O$ 60:40 pH 2.9 with Phosphoric acid | 0.9 and 2.9 (changed at 6.5-7 mins) | 230 | 5, 8, 10, 12, 15, 25, 50 and 100 | ACN:$H_2O$ 60:40 |

The dissolution instrument (DI) was customized to the B.P. 2007 standards, which included dissolution motor and speed controller joined to a stainless steel basket assembly. Paddle speed of 100±0.5 rpm was evaluated with aliquots (5 mL) taken at 0, 15, 30, 45, 60, 75, 90, 105 and 120 minutes. The dissolution assembly was immersed in water bath at 37±0.1° C. Aliquots withdrawn were subjected to drug content analysis after dilution (if required). Corresponding amount of dissolution medium removed was substituted (which has been kept in the same bath to maintain temperature) after each sample collection to maintain the initial volume of the dissolution medium. The aliquots were run in the range of 200-500 nm to record the absorbance.

Methodology

Calibration curves of Antihypertensive drugs and Antilipidemic agents. 1 mM of LOS (0.0423 g) and Val (0.0436 g) were weighed respectively and transferred to separate 100 mL volumetric flasks in simulated gastric medium (SGM) (pH1) and buffers of pH 4, 7.4 and 9. Phosphate buffer of pH 4 and ammonium buffers of pH 7.4 and 9, prepared according to British Pharmacopeia, were used. Volume was made up individually with respective pH medium. Working standard solutions were prepared in the range 0.0075 to 0.03 mM for losartan and 0.0045 to 0.045 mM for valsartan from the primary solutions for all pH medium; Table 2.

TABLE 2

Linearity range for antihypertensive drugs and antilipidemic agents

| Therapeutic Class | Drugs | $\lambda_{max}$ (nm) | Linearity range (mM) |
|---|---|---|---|
| antihypertensive drugs | Losartan | 206 | 0.0075-0.03 |
| | Valsartan | 206 & 250 | 0.0045-0.045 |
| antilipidemic agents | Atorvastatin | 241 | 0.005-0.05 |
| | Pravastatin | 225 | 0.005-0.05 |
| | Simvastatin | 225 & 265 | 0.005-0.05 |

These working standards were run in the region 200-500 nm The $\lambda_{max}$ for losartan appeared at 206 nm in all pH medium; for valsartan it appeared at 207 nm (in medium at pH 1), 206 nm (at pH 4) and 206 and 250 nm (at pH 7.4 and 9). Beer's law obedience was observed by both losartan and valsartan, molar absorptive values were computed in all medium studied. Similarly the calibration curves of Ator, Pra and Sim were also studied in SGM (pH 1) and buffers of pH 4, 7.4 and 9. The concentration range is given in Table 2 above and Tables 3-4.

TABLE 3

Reference standard of antihypertensive drugs in various medium at 206 nm

| | ε ($M^{-1}cm^{-1}$) | | | |
|---|---|---|---|---|
| Conc. M × $10^{-4}$ | pH 1 | pH 4 | pH 7.4 | pH 9 |
| Los 0.075-0.300 | 19840 | 22303 | 21218 | 20382 |
| Val 0.045-0.45 | 41188 | 44450 | 46549 | 66265 |

TABLE 4

Reference standard of antihypertensive drugs in various medium

| Concentration | ε ($M^{-1}cm^{-1}$) | | | |
|---|---|---|---|---|
| 0.5-5M × $10^{-5}$ | pH 1 | pH 4 | pH 7.4 | pH 9 |
| Ator (241 nm) | 53900 | 41000 | 50900 | 50500 |
| Pra (225 nm) | 10200 | 12000 | 600 | 2400 |
| Sim (225 and 265 nm) | 29450 | 16410 | 15770 | 15770 |

Simultaneous method development of Antihypertensive drugs and Antilipidemic agents by RP-HPLC. A RP-HPLC method was developed and studied for validation parameters for the simultaneous quantitative analysis of antihypertensive drugs and antilipidemic agents from bulk drugs and pharmaceutical formulations. Separation was achieved on Beckman ODS-DABS, Ultrasphere™ $C_{18}$ (5µ, 25 cm×4.6 mm) column. 20 µL sample loop was used throughout the experiment. The optimum separation conditions are summarized in Table 1.

Working Standards: 100 µgL$^{-1}$ stock solutions of losartan, valsartan and drugs of selective interacting classes were separately prepared by taking appropriate amount of each drug in their respective diluent; these solutions were further diluted into working solutions to study calibration curve for all drugs (Table 2).

Preparation from dosage forms. Twenty capsules of Cozaar™ containing 50 mg LOS were finely crushed and powder content equivalent to 10 mg of LOS in 100 mL of diluent (acetonitrile:H$_2$O 60:40) was prepared as primary solution. The primary solution was then filtered and standard working solutions were prepared of desire concentrations. Similarly, twenty tablets each of Diovan™ (80 mg VAL), Lipitor™ (20 mg ATR), Lipostat™ (20 mg PRA) and Zocor™ (20 mg SIM) were crushed and weighed separately processed as described above.

Validation of a Simultaneous RP-HPLC Method for Liberation of Antihypertensive Drugs and Antilipidemic Agents System suitability: six replicates of 50 µg/mL of all the analytes were scanned to validate system suitability.

Sensitivity: Signal-to-noise ratio was used to determine limit of detection (LOD) and limit of quantitation (LOQ).

Linearity: Seven concentrations ranges (5 to 100 µg/mL) were used to construct the calibration curve, by plotting the mean peak area of analyte against concentration. Linear regression analysis using least square method was used to measure linearity; Table 5.

TABLE 5

Calibration curves and limits of detection and quantification for antihypertensive drugs and antilipidemic agents

| Drugs | Linear regression equation | LOQ µgmL$^{-1}$ | LOD µgmL$^{-1}$ | r$^2$ |
|---|---|---|---|---|
| Pravastatin | Y = 28827 X + 31927 | 1.02 | 0.31 | 0.9986 |
| Losartan | Y = 45816 X − 8657.2 | 0.49 | 0.14 | 0.9993 |
| Valsartan | Y = 16589 X − 2235.7 | 0.52 | 0.15 | 0.9997 |
| Atorvastatin | Y = 26507 X − 26710 | 0.43 | 0.13 | 0.9981 |
| Simvastatin | Y = 10260 X + 1698.6 | 0.12 | 0.03 | 0.9992 |

Accuracy and precision: Precision of the assay was validated by (intra-day) repeatability and (inter-day) intermediate precision for three successive days. Three different concentrations of analytes (in triplicate) were examined in six autonomous series in the same day for intra-day precision; and for three successive days, daily for inter-day precision (Tables 6-8). The accuracy of the method (proximity b/w the true value and found value), was evaluated as % accuracy=(observed concentration/nominal concentration)×100.

TABLE 6

Accuracy and precision of antihypertensive drugs and antilipidemic agents

| Conc. Inj. µgmL$^{-1}$ | Pravastatin | | Losartan | | Valsartan | | Atorvastatin | | Simvastatin | |
|---|---|---|---|---|---|---|---|---|---|---|
| | % rec | % RSD | % rec | % RSD | % rec | % RSD | % rec | % RSD | % rec | % RSD |
| 5 | 99.5 | 0.32 | 96.48 | 0.6 | 98.38 | 0.88 | 100.6 | 0.48 | 98.98 | 2.6 |
| 10 | 99.21 | 0.5 | 98.47 | 0.98 | 99.76 | 0.98 | 99.09 | 0.92 | 100.2 | 0.25 |
| 15 | 102 | 0.26 | 100.5 | 0.33 | 97.68 | 0.22 | 102 | 0.97 | 100.9 | 0.57 |
| 20 | 99.55 | 0.45 | 100.2 | 1.22 | 100.3 | 1.13 | 100.8 | 1.35 | 101.2 | 2.39 |
| 25 | 100.6 | 0.39 | 98.15 | 1.47 | 99.94 | 1.01 | 98.97 | 0.79 | 100.9 | 1.11 |
| 50 | 100.2 | 0.87 | 99.8 | 0.85 | 100 | 1.19 | 99.66 | 0.7 | 99.75 | 0.78 |
| 100 | 101.9 | 0.86 | 100.3 | 0.88 | 100.4 | 0.7 | 98.39 | 2.3 | 101 | 1.62 |

TABLE 7

Accuracy and precision of antihypertensive drugs and antilipidemic agents in bulk drugs

| % Conc. | Pravastatin | | Losartan | | Valsartan | | Atorvastatin | | Simvastatin | |
|---|---|---|---|---|---|---|---|---|---|---|
| | % rec | % RSD | % rec | % RSD | % rec | % RSD | % rec | % RSD | % rec | % RSD |
| 80 | 101.1 | 1.87 | 100.7 | 0.87 | 99.89 | 1.31 | 99.8 | 0.86 | 100.1 | 1.34 |
| 100 | 99.02 | 0.5 | 98.51 | 0.97 | 101 | 1.36 | 99.92 | 1.19 | 100.1 | 0.17 |
| 120 | 98.65 | 1.39 | 100.1 | 0.73 | 100.1 | 1.44 | 100.5 | 1.57 | 101.8 | 1.66 |

TABLE 8

Accuracy and precision of antihypertensive drugs and antilipidemic agents in pharmaceutical dosage forms

| | Pralip ® 20 mg | | Tancin ® 50 mg | | Diovan ® 80 mg | | Derot ® 10 mg | | Limitrol ® 20 mg | |
|---|---|---|---|---|---|---|---|---|---|---|
| Tablet | % rec | % RSD | % rec | % RSD | % rec | % RSD | % rec | % RSD | % rec | % RSD |
| 1 | 99.62 | 0.66 | 99.47 | 0.52 | 100.6 | 0.55 | 101.2 | 0.41 | 100.6 | 0.96 |
| 2 | 101.2 | 0.47 | 99.35 | 0.84 | 101.2 | 0.48 | 99.48 | 0.552 | 100.9 | 0.84 |
| 3 | 98.67 | 1.22 | 98.33 | 1.11 | 99.62 | 0.86 | 99.36 | 0.95 | 100.3 | 0.93 |
| 4 | 99.27 | 0.65 | 100.5 | 1.3 | 98.48 | 1.34 | 99.75 | 0.74 | 98.96 | 0.55 |
| 5 | 100.4 | 0.82 | 98.98 | 0.52 | 100.2 | 0.92 | 100.2 | 1.36 | 99.66 | 0.75 |
| Mean | 99.84 | 0.764 | 99.32 | 0.858 | 100 | 0.83 | 100 | 0.802 | 100.1 | 0.806 |
| STDEV | 1.003 | 0.283 | 0.781 | 0.349 | 1.045 | 0.342 | 0.754 | 0.371 | 0.789 | 0.165 |
| RSD | 1.005 | 37.1 | 0.786 | 40.7 | 1.044 | 41.3 | 0.751 | 46.35 | 0.788 | 2.47 |

Specificity: Detection of all the analytes was carried out in presence of different excipients. Selectivity and specificity was assessed by cancelling out the possible interference resulting from excipients found in the pharmaceutical dosages. Placebo working solutions of dosage sample was prepared by mixing respective excipients for analysis, such as: aerosol, carboxymethylcellulose, croscarmelose sodium, dicalcium phosphate, hydroxypropylcellulose, hydroxypropylmethylcellulose, magnesium stearate, monohydrated lactose, neutral talc, polyethylenglycol 400, polyoxyl stearate and starch. A typical chromatogram is presented in the FIG which clearly shows the separation of all the drugs.

Drug-Drug Interaction Studies of Antihypertensive Drugs and Antilipidemic Agents Interaction Studies Using UV/Visible Spectrophotometry Availability Studies. Before assessment of drug-drug interaction, the availability of antihypertensive drugs and antilipidemic agents was independently evaluated in SGM and in buffers of pH 4, 7.4 and 9 on a customized B.P. DI. For each set of experiments, each tablet was added to 500 mL dissolution medium at pH 1, 4, 7.4 or 9 maintained at 37° C. Samples of 5 mL were extracted at zero minute and then periodically after fifteen minute periods for 2 hours. A corresponding volume of same medium kept at same temperature was substituted for removed samples. The percentage of drug released was quantitated spectrophotometrically at the $\lambda_{max}$ of the drugs using respective pH medium as blank; see FIGS. 2-6.

In FIG. 2 samples were drawn from the medium using a pipette and were filtered. The 5 mL samples were withdrawn and corresponding volume of same medium kept at same temperature was substituted for removed samples.

In FIG. 5, samples were drawn from the medium using a pipette and were filtered. The 5 mL samples were withdrawn and corresponding volume of same medium kept at same temperature was substituted for removed samples. The drug release maximum 43-49 percent in the acidic medium and after that with each withdrawn sample, the total drug in the medium is diluted.

Interaction studies by UV/Visible spectrophotometry. In vitro interaction studies of antihypertensive drugs and antilipidemic agents were studied individually by using different kinds of dissolution media: SGM and media at pH 4, 7.4 and 9 as described in the experimental section.

In each set of experiments losartan or valsartan was initially added at 0 min to 500 mL dissolution medium SGM or media at pH 4, 7.4 and 9 already maintained at 37° C. The second drug, statin (ATOR, PRA or SIM) was added at the same time at zero mins. 5 mL samples were collected at regular intervals for 2 hours. The drug contents (losartan in presence of respective interacting drug, and valsartan in presence of respective interacting drug) were quantified spectrophotometrically at their respective $\lambda_{max}$ by employing simultaneous equations; FIGS. 7-12.

In FIG. 7, the drug contents (losartan in presence of respective interacting drug) were quantified spectrophotometrically at their respective $\lambda_{max}$ by employing simultaneous equations, that is, by using the molar absorptive value of the drug at a particular wavelength and a particular pH. It is clearly visible from the data that the drugs, when given together interact with each other and form a complex that has molar absorptive value different than the original drug, hence the unreasonably high values. The high value at LOS (higher than 100%) shows that the complex that is formed has a high absorption at the wavelength of losartan while the high value of statin represent that the complex absorbs near statin's $\lambda_{max}$.

The data in FIG. 7 suggest that the LOS and ATR should not be given together as these orally-administered drugs when given together may interact in the digestive tract. To avoid interaction, the drugs may be orally administered 2 to 3 hours apart. In FIG. 7, the expected values range from zero to 100 percent of available losartan (equivalent to the 50 mg tablet used). The high value shows that the drugs have undergone interaction and therefore are not available as their original molecule that can be quantitated at their respective $\lambda_{max}$.

The data in FIG. 8 suggest that the LOS and PRA should not be given together as these orally-administered drugs when given together may interact in the digestive tract. To avoid interaction, the drugs may be orally administered 2 to 3 hours apart.

In FIG. 9, when the losartan value is zero, this means that the drug has undergone chemical changes and is not available as losartan. Also, when SIM is available more than 100 percent, it means that it is also changed and not available as simvastatin. The complex that has formed absorbs more at the wavelength of simvastatin therefore high values of SIM. Both of the drugs are NOT available in their original form. The data in FIG. 9 suggest that the LOS and SIM should not be co-administered as these orally-administered drugs when given together may interact in the digestive tract. To avoid interaction, the drugs may be orally administered 2 to 3 hours apart.

The data in FIG. 10 suggest that the VAL and ATR should not be given together as these orally-administered drugs when given together may interact in the digestive tract. To avoid interaction, the drugs may be orally administered 2 to 3 hours apart.

The data in FIG. 11 suggest that the VAL and PRA should not be given together as these orally-administered drugs when given together may interact in the digestive tract. To avoid interaction, the drugs may be orally administered 2 to 3 hours apart.

The data in FIG. 12 suggest that the VAL and SIM should not be co-administered as these orally-administered drugs when given together may interact in the digestive tract. To avoid interaction, the drugs may be orally administered 2 to 3 hours apart.

As the spectra of the two interacting drugs fused with each other, simultaneous methods were developed to determine losartan/valsartan and drugs of interacting classes along with each other. This technique enables one to quantitate the content of the two drugs co-existing in the same medium, without needing to separate them. To achieve this, molar absorptivity values of both losartan and the respective interacting drug were calculated at $\lambda_{max}$ of their own and at the $\lambda_{max}$ of each other using their calibration curves standards in all four pH medium.

Illustratively, losartan and atorvastatin absorb at 206 and 241 nm respectively in SGM. A mathematical relationship gives the concentration of these drugs simultaneously, when measured at their respective $\lambda_{max}$. Molar absorptivity values were used to quantitate these drugs in the solution of unknown concentrations.

According to Beer's law:

$$A = \varepsilon bc \text{ or } \varepsilon = A/bc \tag{1}$$

(A=absorbance, $\varepsilon$=molar absorptivity or epsilon, b=path length of the cell (=1 cm), and c=concentration of solution). If more than one component were present in a solution, which absorbs at the same wavelength, then the above equation would be written as:

$$A_{206} = \varepsilon C_1 + \varepsilon' C_2 \tag{2}$$

($C_1$ and $C_2$=concentrations of two drugs present in the solution, $\varepsilon$ and $\varepsilon'$=the absorptive values of the two drugs, obtained from the calibration curves).

Losartan and atorvastatin absorb maximum at 206 nm and 241 nm respectively. Let $C_1$ and $C_2$ be the respective concentrations of losartan and atorvastatin. Now equation 2 can be written as:

$$A_{206} = a_1 C_1 + b_1 C_2 \tag{3}$$

$$A_{241} = a_2 C_1 + b_2 C_2 \tag{4}$$

($a_1$ and $a_2$=molar absorptive value of losartan at 206 and 241 nm, $b_1$ and $b_2$=molar absorptive values of atorvastatin at 206 and 241 nm)

By multiplying equation 3 with $a_2$ and equation 4 with $a_1$:

$$C_2 = \frac{A_{206} a_2 - A_{241} a_1}{a_2 b_1 - a_1 b_2} \tag{5}$$

Similarly, $$C_1 = \frac{A_{206} b_2 - A_{241} b_1}{a_1 b_2 - a_2 b_1} \tag{6}$$

By employing Equations 5 and 6, amounts of losartan and atorvastatin simultaneously present in the same medium were quantitated. The rest of the interactions of losartan and valsartan with interacting drugs were similarly determined.

Interaction studies using RP-HPLC. The newly developed method of antihypertensive drugs and antilipidemic agents was applied to assess sartan/statin drug interactions. 100 $\mu gmL^{-1}$ solutions of losartan or valsartan and interacting drugs were prepared individually in SGM (pH 1) and in buffer medium at pH 4, 7.4 and 9. The solutions of losartan or valsartan and interacting drugs were mixed in equal proportion by weight in round bottomed flasks and refluxed for 3 hours. Aliquots of 2 mL were drawn from the reaction flask at 0 min and then after an interval of 30 minutes for three hours. Aliquots were filtered through a Millipore filter (0.45 μm) and analyzed by RP-HPLC using the developed method; see FIGS. 13-18.

In FIGS. 13-18, which assess drug interaction via HPLC, a different method was utilized that did not use tablets and 100 $\mu gmL^{-1}$ solutions of the two interacting drugs were prepared individually in SGM (pH 1) and in buffer medium at pH 4, 7.4 and 9; and mixed to study the interaction. The drugs are 100 percent available at the zero minute. Interactions were assessed by measuring a decrease in availability. Since HPLC is a more specific technique, the eluted peaks at the retention time of the drugs only quantitate the drug and not the resulting complex. The values mentioned in FIGS. 13-18 represent drug interactions but the resulting complex is unstable and is subject to deteriorating which explains how values of each of the two drugs can either increase or decrease.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for simultaneously quantifying amounts of a dissolved sartan and dissolved statin in a mixture containing at least one sartan and at least one statin, comprising:
    contacting known amounts of at least one sartan and at least one statin with one or more solvents to form the mixture,
    removing undissolved material from the mixture, applying the resulting mixture to a RP-HPLC column in a mobile phase comprising acetonitrile and water in a ratio of no greater than 70:30;
    quantifying amounts of the at least one sartan and the at least one statin dissolved in the mixture by their UV absorption at 220-240 nm; and
    comparing the UV elution profile of the at least one sartan and the at least one statin dissolved in the mixture to individual control profiles of the at least one sartan and the at least one statin,
    wherein the at least one sartan and the at least one statin dissolved in the mixture contains at least one of losartan or valsartan and at least one of atorvastatin, pravastatin or simvastatin and wherein losartan has a concentration of 0.0075-0.03 mM, valsartan has a concentration of 0.0045-0.045 mM, atorvastatin has a concentration of 0.005-0.05 mM, pravastatin has a concentration of 0.005-0.05 mM and simvastatin has a concentration of 0.005-0.005 mM, when present in the mixture.

2. The method of claim 1, wherein applying the mixture is performed using a mobile phase of acetonitrile to water of no more than 60:40 and wherein quantifying the at least one sartan and at least one statin in the mixture is by UV absorption at 225-235 nm.

3. The method of claim 1, wherein applying the mixture is performed using a mobile phase of acetonitrile to water of about 60:40 and wherein quantifying the at least one sartan and at least one statin in the mixture is by UV absorption at about 230 nm.

4. The method of claim 1, wherein the solvent has a pH of no more than 4.

5. The method of claim 1, wherein the solvent has a pH of more than 4 and no more than 7.

6. The method of claim 1, wherein the solvent has a pH of more than 7, but no more than 9.

7. The method of claim 1, wherein the at least one sartan and at least one statin comprises losartan and at least one of atorvastatin, pravastatin or simvastatin.

8. The method of claim 1, wherein the at least one sartan and at least one statin comprises losartan and at least two of atorvastatin, pravastatin or simvastatin.

9. The method of claim 1, the at least one sartan and at least one statin comprises losartan, atorvastatin, pravastatin and simvastatin.

10. The method of claim 1, wherein the at least one sartan and at least one statin comprises valsartan and at least one of atorvastatin, pravastatin or simvastatin.

11. The method of claim 1, wherein the at least one sartan and at least one statin comprises valsartan and at least two of atorvastatin, pravastatin or simvastatin.

12. The method of claim 1, wherein the at least one sartan and at least one statin comprises valsartan and atorvastatin, pravastatin and simvastatin.

13. A method for simultaneously quantifying dissolved amounts of dissolved sartan and dissolved statin in a mixture containing at least one sartan and at least one statin, comprising:
    contacting known amounts of the at least one sartan and the at least one statin with one or more solvents to form the mixture,
    removing undissolved material from the mixture, applying the resulting mixture to a RP-HPLC column in a mobile phase comprising acetonitrile and water in a ratio of no greater than 70:30;
    quantifying amounts of the at least one sartan and the at least one statin dissolved in the mixture by their UV absorption at 220-240 nm; and
    comparing the UV elution profile of the at least one sartan and the at least one statin dissolved in the mixture to individual control profiles of the at least one sartan and the at least one statin,
    wherein said known amounts of the at least one sartan and the at least one statin are contacted with at least two different solvents having different pHs, and wherein the dissolved amounts of the at least one dissolved sartan and the at least one dissolved statin are quantified in each solvent.

14. The method of claim 13, wherein the at least one sartan and at least one statin are contacted with solvents at pH 1, 4, 7.4 and 9 and wherein amounts of the at least one sartan and at least one statin are quantified in each solvent.

15. The method of claim 13, further comprising selecting or adjusting a drug regimen that comprises coadministration of the at least one sartan and at least one statin by selecting safe and effective dosages of the sartan and statin based on the amounts of sartan and dissolved in the solvents.

16. The method of claim 13, further comprising selecting a drug formulation providing safe and effective dosages of the at least one sartan and at least one statin based on the amounts of sartan and statin dissolved in the solvents.

17. The method of claim 16, wherein said drug formulation is formulated to release the at least one sartan and the at least one statin into the same gastric or luminal compartment.

18. The method of claim 16, wherein said drug formulation is formulated to release the at least one sartan in an acidic gastric compartment and the at least one statin in an alkaline luminal compartment, or vice versa.

19. The method of claim 18, wherein said drug formulation reduces an amount of the sartan and/or statin needed for efficacy compared to a drug formulation where both sartan and statin are released into the same compartment.

* * * * *